(12) United States Patent
Looman

(10) Patent No.: US 11,906,866 B2
(45) Date of Patent: Feb. 20, 2024

(54) ELECTROCHROMIC FILMS AND METHODS OF FORMING AND USING

(71) Applicant: Gentex Corporation, Zeeland, MI (US)

(72) Inventor: Steven D. Looman, Holland, MI (US)

(73) Assignee: GENTEX CORPORATION, Zeeland, MI (US)

( * ) Notice: Subject to any disclaimer, the term of this patent is extended or adjusted under 35 U.S.C. 154(b) by 601 days.

(21) Appl. No.: 16/911,448

(22) Filed: Jun. 25, 2020

(65) Prior Publication Data

US 2020/0409225 A1 Dec. 31, 2020

Related U.S. Application Data

(60) Provisional application No. 62/867,385, filed on Jun. 27, 2019.

(51) Int. Cl.
*G02F 1/1516* (2019.01)
*G02B 5/30* (2006.01)
(Continued)

(52) U.S. Cl.
CPC ...... *G02F 1/15165* (2019.01); *B32B 17/1022* (2013.01); *B32B 17/10036* (2013.01);
(Continued)

(58) Field of Classification Search
CPC . G02F 1/15165; G02B 5/3058; C07D 213/22; C07D 241/48; B60R 1/088
See application file for complete search history.

(56) References Cited

U.S. PATENT DOCUMENTS 5,928,572 A 7/1999 Tonar et al.
5,940,201 A 8/1999 Ash et al.
(Continued)

FOREIGN PATENT DOCUMENTS

WO 9842796 A1 10/1998
WO 9902621 A1 1/1999
WO 2011068852 A1 6/2011

OTHER PUBLICATIONS

Roger J. Mortimer, David R. Rosselinsky, and Paul M.S. Monk, Electrochromic Materials and Devices, 2015, 9 pages, Willey-VCH Verlag Gmbh & Co, KGaA, Weinheim, Germany.
(Continued)

*Primary Examiner* — Bijan Ahvazi
(74) *Attorney, Agent, or Firm* — Price Heneveld LLP; Brian James Brewer

(57) ABSTRACT

An electro-optic element includes a first electroactive film including a first electroactive component sequestered adjacent to a first electrically conductive layer and a second electroactive film including a second electroactive component sequestered adjacent to a second electrically conductive layer. At least one of the first electroactive film and the second electroactive film is capable of reversibly attenuating transmittance of light having a wavelength within a predetermined wavelength range. The first electroactive component can include a first oxidation state and at least a second oxidation state. An amount of the first electroactive component relative to the second electroactive component can be configured to limit formation of the second oxidation state of the first electroactive component.

20 Claims, 9 Drawing Sheets

(51) Int. Cl.
*C07D 213/22* (2006.01)
*C07D 241/48* (2006.01)
*C09K 9/02* (2006.01)
*B32B 17/10* (2006.01)
*B60R 1/08* (2006.01)

(52) U.S. Cl.
CPC .. *B32B 17/10321* (2013.01); *B32B 17/10403* (2013.01); *B32B 17/10495* (2013.01); *C07D 213/22* (2013.01); *C07D 241/48* (2013.01); *C09K 9/02* (2013.01); *G02B 5/3058* (2013.01); *G02F 1/1516* (2019.01); *B60R 1/088* (2013.01); *C09K 2211/1022* (2013.01); *G02F 2201/44* (2013.01)

(56) References Cited

U.S. PATENT DOCUMENTS

| | | | |
|---|---|---|---|
| 5,998,617 | A | 12/1999 | Srinivasa et al. |
| 6,020,987 | A | 2/2000 | Baumann et al. |
| 6,037,471 | A | 3/2000 | Srinivasa et al. |
| 6,137,620 | A | 10/2000 | Guarr et al. |
| 6,141,137 | A | 10/2000 | Byker et al. |
| 6,193,912 | B1 | 2/2001 | Thieste et al. |
| 6,241,916 | B1 | 6/2001 | Claussen et al. |
| 6,245,262 | B1 | 6/2001 | Varaprasad et al. |
| 6,249,369 | B1 | 6/2001 | Theiste et al. |
| 6,268,950 | B1 | 7/2001 | Ash et al. |
| 6,519,072 | B2 | 2/2003 | Nishikitani et al. |
| 6,635,194 | B2 | 10/2003 | Kloeppner et al. |
| 7,001,540 | B2 | 2/2006 | Kloeppner et al. |
| 8,282,253 | B2 | 10/2012 | Lynam |
| 9,964,828 | B2 | 5/2018 | Theiste et al. |
| 2015/0346573 | A1* | 12/2015 | Theiste ................ H01G 11/04 429/188 |
| 2017/0320441 | A1* | 11/2017 | Luten ................ G02F 1/133536 |
| 2018/0095338 | A1* | 4/2018 | Ash ...................... C07D 213/22 |
| 2019/0204702 | A1 | 7/2019 | Kloeppner et al. |

OTHER PUBLICATIONS

Richard J. Bushby, Stephen M. Kelly, and Mary O'Neill (Editors), Liquid Crystalline Semiconductors, Materials, Properties ad Applications, Springer Series in Materials Science 169, 2013, 15 pages, Published by Springer, The Netherlands.

Elda Hegmann, The 2017 International Liquid Crystal Elastomers Conference (2017 ILEC), Liquid Crystals Today, 2018, vol. 27, No. 2, 25-27, Taylor & Francis Group, United Kingdom, https://doi.org/10.1080/1358314X.2018.1479159.

Koen Binnemans, Ionic Liquid Crystals, Chemical Reviews, Nov. 9, 2005, 2 pages, vol. 105, No. 11.

Danqing Liu, and Dirk J. Broer, Liquid Crystal Polymer Networks: Preparation, Properties, and Applications of Films with Patterned Molecular Alignment, Langmuir 2014, 30 13499-13509, ACS Publications.

Daichi Yamaoka, Mitsuo Hara, Shusaku Nagano, and Takahiro Seki, Photoalignable Radical Initiator for Anisotropic Polymerization in Liquid Crystalline Media, Macromolecules, 2015, 48, 908-914, ACS Publications.

Martin Schadt, Hubert Seiberle, Andreas Schuster and Stephen M. Kelly, Photo-Generation of Linearly Polymerized Liquid Crystal Aligning Layers Comprising Novel, Integrated Optically patterned Retarders and Color Filters, Jpn. J. Appl. Phys. vol. 34 (1995), pp. 3240-3249, Part 1, No. 6A, Jun. 1995.

* cited by examiner

ELECTROCHROMIC FILMS AND METHODS OF FORMING AND USING

CROSS-REFERENCE TO RELATED APPLICATIONS

This application claims priority to and the benefit under 35 U.S.C. § 119(e) of U.S. Provisional Application No. 62/867,385, filed on Jun. 27, 2019, entitled ELECTROCHROMIC FILMS AND METHODS OF FORMING AND USING, the disclosure of which is hereby incorporated herein by reference in its entirety.

FIELD OF THE DISCLOSURE

The present disclosure generally relates to an electro-optic element, and more particularly to electrochromic films for use in electro-optic elements and devices.

SUMMARY OF THE DISCLOSURE

According to one aspect of the present disclosure, an electro-optic element includes a cathodic film and an anodic film. The cathodic film can include a cathodic component sequestered adjacent to a first electrically conductive layer by a first polymer matrix. The anodic film can include an anodic component sequestered adjacent to a second electrically conductive layer by a second polymer matrix. At least one of the cathodic film and the anodic film is capable of reversibly attenuating transmittance of light having a wavelength within a predetermined wavelength range. The cathodic film and anodic film can be configured such that the cathodic component is present in excess relative to the anodic component.

According to an aspect of the present disclosure, an electro-optic element includes a first electroactive film and a second electroactive film. The first electroactive film can include a first electroactive component sequestered adjacent to a first electrically conductive layer. The first electroactive component can include a first oxidation state and at least a second oxidation state. The second electroactive film can include a second electroactive component sequestered adjacent to a second electrically conductive layer. At least one of the first electroactive film and the second electroactive film is capable of reversibly attenuating transmittance of light having a wavelength within a predetermined wavelength range. An amount of the first electroactive component relative to the second electroactive component can be configured to limit formation of the second state of the first electroactive component.

According to an aspect of the present disclosure, a method of forming an electro-optic element is provided. The method can include providing a first electroactive film that includes a first electroactive component sequestered adjacent to a first electrically conductive layer. The first electroactive component can include a first oxidation state and at least a second oxidation state. A second electroactive film including a second electroactive component sequestered adjacent to a second electrically conductive layer can also be provided. At least one of the first electroactive film and the second electroactive film is capable of reversibly attenuating transmittance of light having a wavelength within a predetermined wavelength range. An amount of the first electroactive component relative to the second electroactive component can be provided to limit formation of the second oxidation state of the first electroactive component.

These and other features, advantages, and objects of the present disclosure will be further understood and appreciated by those skilled in the art by reference to the following specification, claims, and appended drawings.

BRIEF DESCRIPTION OF THE DRAWINGS

The present disclosure will become more fully understood from the detailed description and the accompanying drawings, wherein.

DETAILED DESCRIPTION

Figure 1:
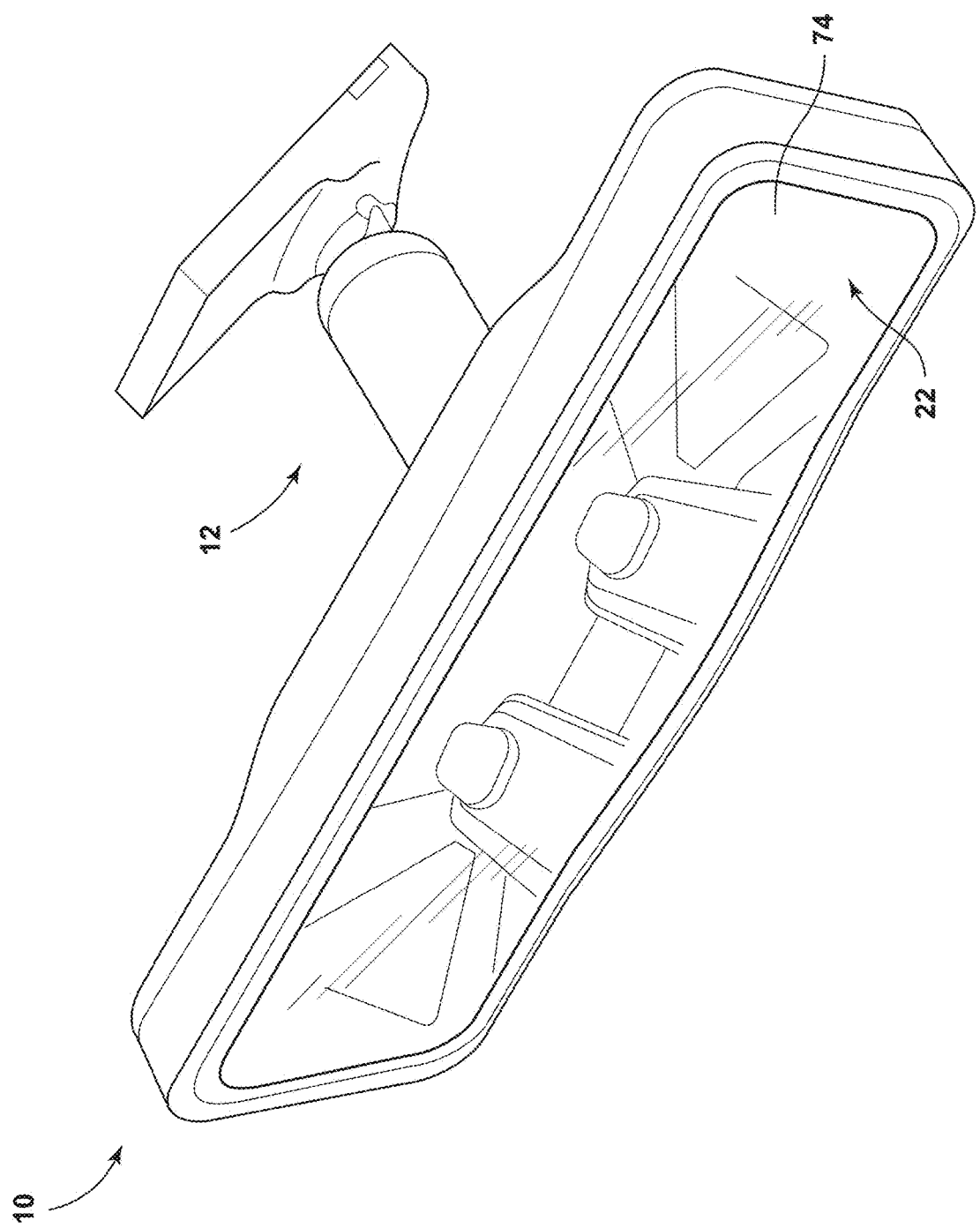
FIG. 1 is a top-down perspective view of a rearview mirror assembly, according to an aspect of the present disclosure.

The present illustrated aspects reside primarily in combinations of method steps and apparatus components related to electrochromic films for use in electro-optic elements and devices. Accordingly, the apparatus components and method steps have been represented, where appropriate, by conventional symbols in the drawings, showing only those specific details that are pertinent to understanding the aspects of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to the surface of the device closer to an intended viewer of the device, and the term "rear" shall refer to the surface of the device further from the intended viewer of the device. However, it is to be understood that the disclosure may assume various alternative orientations, except where expressly specified to the contrary. It is also to be understood that the specific devices and processes illustrated in the attached drawings, and described in the following specification are simply exemplary aspects of the inventive concepts defined in the appended claims. Hence, specific dimensions and other physical characteristics relating to the aspects disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

As used herein, the term "and/or," when used in a list of two or more items, means that any one of the listed items can be employed by itself, or any combination of two or more of the listed items, can be employed. For example, if a composition is described as containing components A, B, and/or C, the composition can contain A alone; B alone; C alone; A and B in combination; A and C in combination; B and C in combination; or A, B, and C in combination.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Referring to FIGS. 1-5B, aspects of the present disclosure relate to electrochromic films for electro-optic elements and devices incorporating said electro-optic elements that include a cathodic component and an anodic component that undergo reduction-oxidation reactions upon application of an electrical potential that changes a transmission, absorption, and/or reflection characteristic of the electro-optic element. According to an aspect of the present disclosure, the relative amounts of the cathodic component and the anodic component can be selected to inhibit formation of a particular oxidation state of either the cathodic or the anodic component.

According to one aspect of the present disclosure, a first electroactive film including a first electroactive component sequestered adjacent to a first electrically conductive layer by a first polymer matrix and a second electroactive film including a second electroactive component sequestered adjacent a second electrically conductive layer by a second polymer matrix. The first electroactive film can be a cathodic film including a cathodic component as the first electroactive component and the second electroactive film can be an anodic film including an anodic component as the second electroactive component and vice versa. The first and/or second electroactive films can be capable of reversibly attenuating transmittance of light having a wavelength within a predetermined range when a potential is applied across the device and/or between the first electrically conductive layer and the second electrically conductive layer. The first and second electroactive films can be configured such that one of the cathodic component or the anodic component is present in excess relative to the other.

In one aspect, the cathodic film can be configured to provide the cathodic component in excess relative to the anodic component such that the formation of a particular oxidation state of the cathodic component is decreased. In another aspect, the anodic film can be configured to provide the anodic component in excess relative to the cathodic component such that the formation of a particular oxidation state of the anodic component is decreased. According to an aspect of the present disclosure, whichever component (i.e., the cathodic component or the anodic component) has a less stable second oxidation state is provided in excess to decrease formation of the less stable oxidation state.

Figure 2:
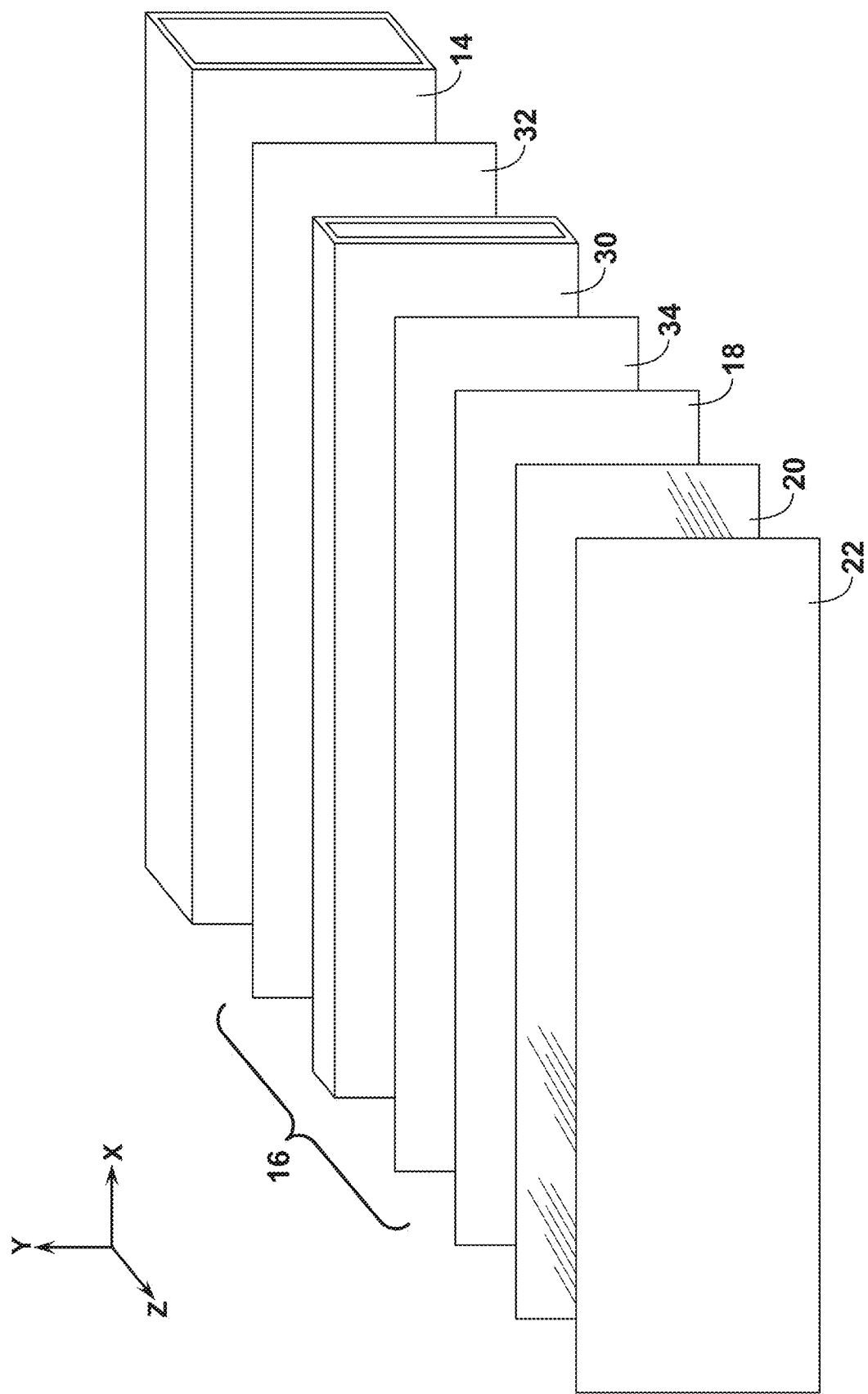
FIG. 2 is a partially exploded view of the rearview mirror assembly of FIG. 1, according to an aspect of the present disclosure.

Referring now to FIGS. 1 and 2, the illustrated rearview mirror assembly 10 can be an interior rearview assembly positioned within an interior of a vehicle. When the rearview mirror assembly 10 is an interior rearview assembly, the rearview mirror assembly 10 may be connected to a mount 12, which is adapted to be mounted inside the vehicle in a location proximate to or on a front windshield of the vehicle. While aspects of the present disclosure are described in the context of a rearview mirror assembly, the aspects of the present disclosure are also applicable in other optical assemblies, non-limiting examples of which include interior and exterior mirrors, architectural windows, vehicle windows, sunroofs, aircraft windows, heads-up displays, displays, camera filter, camera shutter, and eyewear, as well as other optical assemblies positioned within bezels and housings.

The mirror assembly 10 includes, in order from a rear position (e.g., vehicle forward) to a front position (e.g., vehicle rearward), a light source 14, a display 16, an optional substrate 18, an optional reflective polarizer 20, and an electro-optic element 22. It will be understood that different and/or additional components may be used in the assembly, depending on the particular application. It will be understood that the reflective polarizer 20 may be positioned on either a vehicle-forward or vehicle-rearward surface of the optional substrate 18 without departing from the teachings provided herein. The light source 14, or light engine, is configured to backlight the display 16 by providing light to a rear of the display 16. Light from the light source 14 moves in a Z-direction through the rearview mirror assembly 10, through the display 16, and toward the electro-optic element 22. In the depicted example, the display 16 is a liquid crystal display incorporating a liquid crystal medium 30 disposed between two polarizers, an entrance polarizer 32 and an exit polarizer 34. However, it will be understood that aspects of the present disclosure can be used in mirrors and any other suitable devices that do not include polarizers. The light source 14 and/or display 16 may extend the entire length of the rearview mirror assembly 10 creating a "full-display" assembly, or may only extend a portion of the length. It will be appreciated, however, that a concept of a "full-display" assembly, where the display 16, or a plurality of displays, located behind the electro-optic element 22, overlaps in projection onto a viewable surface of assembly 10, with most or all of this viewable surface, is also contemplated by the various examples of this disclosure. The display 16 and/or light source 14 may be angled (e.g., about 3° to about 5°) relative to the reflective polarizer 20 and optionally include an optical bonding adhesive disposed between display 16, the reflective polarizer 20, the optional substrate 18 and other locations.

The entrance and/or exit polarizers 32, 34 may include a reflective polarizer which may be a linear polarizer, an elliptical polarizer or a circular polarizer and might include an optical retarder such as a quarter-wave plate or a half-wave plate. A wire-grid polarizer provides one example of a reflective polarizer that may be used for the entrance and/or exit polarizers 32, 34. Alternatively, a reflective polarizer may include a polymer-based film structure including at least one optically anisotropic layer. Such polymer-based film structure is generally referred to herein as an anisotropic polymer-based film (APBF). Non-limiting examples of APBFs are provided by a multilayered polymer film, including a body of alternating layers of a crystalline-based polymer and another selected polymer, or by micro-structured film-based polarizers, such as brightness enhancement films, or by dual brightness enhancement films.

Positioned vehicle rearward of the display 16 is the optional substrate 18 and the reflective polarizer 20. The optional substrate 18 may be a piece of glass, polymer or other sufficiently optical clear component configured to transmit light from the display 16. The reflective polarizer 20 may be positioned on the substrate 18 (e.g., on a vehicle forward or vehicle rearward surface). In a specific example, the reflective polarizer 20 may be laminated onto a surface of the substrate 18.

Figure 3A:
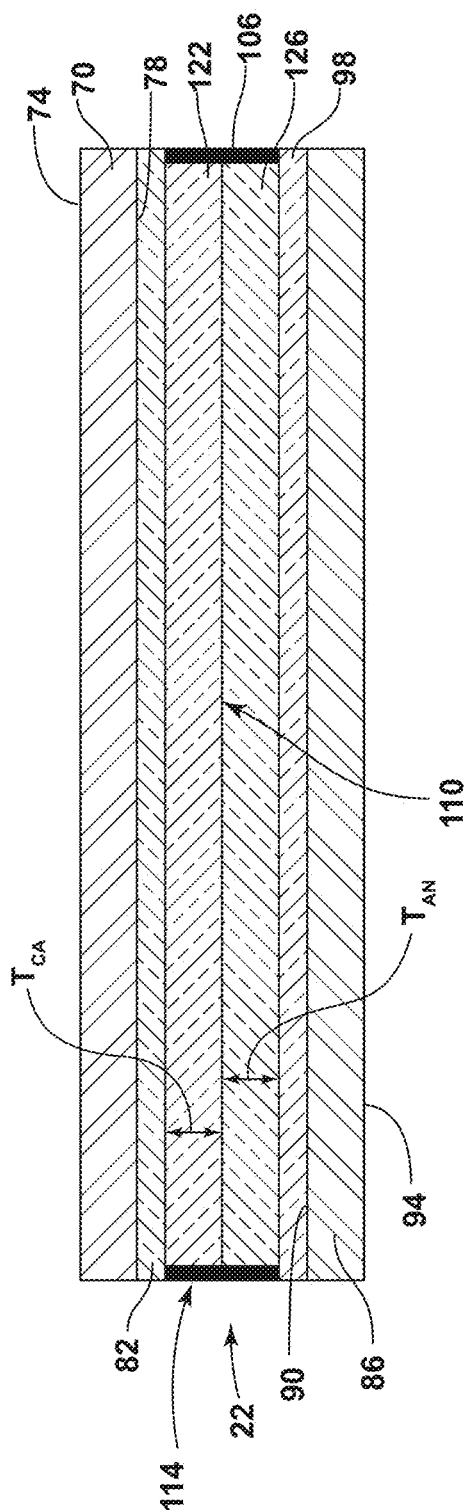
FIG. 3A is a cross-sectional view of an electro-optic element, according to an aspect of the present disclosure.
Figure 3B:
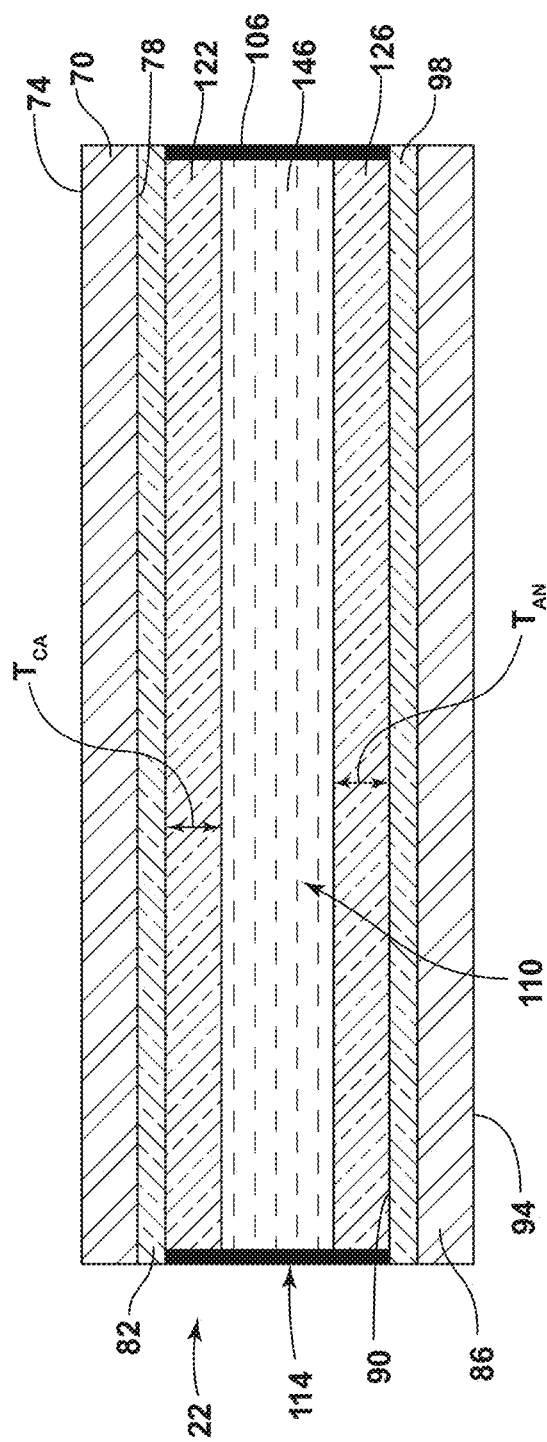
FIG. 3B is a cross-sectional view of an electro-optic element, according to an aspect of the present disclosure.

Referring now to FIGS. 2 and 3A-B, disposed vehicle rearward of the reflective polarizer 20 is the electro-optic element 22. The electro-optic element 22 is operable between a substantially clear state and a substantially dark or darkened state, as well as intermediate states thereto. The darkened state of the electro-optic element 22 is defined relative to the transmissivity of the substantially clear state. Typical transmissivity of the electro-optic element 22 in the substantially clear state may be greater than about 25%, greater than about 50%, greater than about 55%, or greater than about 85%. The percentage of reflectance, transmittance, and absorbance of the electro-optic element 22 sum to 100%. Typical transmissivity of the electro-optic element 22 in the substantially darkened state may be less than about 10% less than about 1%, less than about 0.1%, or less than about 0.01%.

The electro-optic element 22 includes a first substrate 70 having a front or first surface 74 and a second surface 78. The first surface 74 is a viewer side and is the vehicle rearward, or viewer facing side, of the rearview mirror assembly 10 (FIG. 1). In some examples, an anti-reflection layer may be disposed over part or the entirety of the first surface 74. A first electrically conductive layer 82 is positioned on the second surface 78. The electro-optic element 22 includes a second substrate 86. The second substrate 86 includes a third surface 90 and a fourth surface 94. A second electrically conductive layer 98 is positioned on the third surface 90. The fourth surface 94 of the second substrate 86 is an inward, or vehicle forward, facing surface (e.g., adjacent the reflective polarizer 20). It should be noted that the first or second substrates 70, 86 may be larger than one another or the first or second substrates 70, 86 may not be completely adjacent to one another to create an offset along at least a portion of the perimeter of the electro-optic element 22. Further, in examples not including the optical substrate 18, the reflective polarizer 20 may be positioned on the third surface 90 or the fourth surface 94 of the electro-optic element 22 without departing from the aspects provided herein. The first and second substrates 70 and 86 can be made of glass, plastic, or other optically transparent or translucent material.

The first and second substrates 70, 86 can optionally have a thickness of less than about 1.2 mm, less than about 0.8 mm, or less than about 0.6 mm. However, the thickness of the first and second substrates 70, 86 may vary depending on the end use optical assembly. A second electrically conductive layer 98 is positioned on the third surface 90. In various aspects, the second electrically conductive layer 98 may include a metal reflector or one or more coatings configured as a transmissive, reflective, partially reflective, partially transmissive ("transflective") coating. Further, in examples utilizing the reflective polarizer 20 on the third surface 90, the reflective polarizer 20 may be a wire-grid polarizer and function as the second electrically conductive layer 98 without departing from the teachings provided herein. Inclusion of a metal reflector or a transflective coating may render the electro-optic element 22 at least partially reflective.

Still referring to FIGS. 2 and 3A-B, a primary seal 106 traverses an approximate perimeter of, and is configured to cooperate with, the first and second substrates 70, 86 to define a cavity 110 as substantially hermetic. The primary seal 106 may be applied to the first or second substrates 70, 86 by methods commonly used in the liquid crystal display (LCD) industry, such as by silk-screening or dispensing. In one example, the primary seal 106 may incorporate a first and a second seal as components of the primary seal 106. An electro-optic structure 114 is disposed within the cavity 110. In one example, first and second annular bands of highly conductive material are optionally deposited around the perimeter of the first and second substrates 70, 86, respectively, and in electrical contact with first electrically conductive layer 82 and the second electrically conductive layer 98. Additionally, electrically-conducting structures (e.g., clips or wires) are secured to the highly conductive material and spatially separated from one another. The electrically-conducting structures may supply an electrical voltage to the first and second annular bands of highly conductive material to create a voltage across the electro-optic structure 114, through the first and second electrically conductive layers 82 and 98, respectively, thereby reversibly electrically driving the electro-optic element 22 between the substantially dark and substantially clear states. The first and second annular bands of highly conductive material may include silver, gold or aluminum (such as, for example, in a form of metallic flakes or particles dispersed in a hosting material).

According to one aspect of the present disclosure, the electro-optic structure 114 is an electrochromic structure which includes at least one solvent, at least one anodic film 126 that contains at least one anodic component, and at least one cathodic film 122 that contains at least one cathodic component. The electro-optic structure 114 may also contain a solvent or plasticizer. It will be understood that the anodic and cathodic components may alternatively be referred to as chromophores or electrochromic molecules. Further, it will be understood that the anodic and/or cathodic components may be part of a polymer or a monomer. Typically, both of the anodic and cathodic components are electroactive and at least one of them is electrochromic. It will be understood that regardless of its ordinary meaning, the term "electroactive" may mean a material that undergoes a modification in its oxidation state upon exposure to a particular electrical potential difference. Additionally, it will be understood that the term "electrochromic" may mean, regardless of its ordinary meaning, a component or material that exhibits a change in its extinction coefficient at one or more wavelengths upon exposure to a particular electrical potential difference. Electrochromic components, as described herein, include materials whose color or opacity are affected by an electrical current, such that when an electrical field is applied to the material, the color or opacity changes from a first phase to a second phase. The electrochromic component may be a single-layer, single-phase component, multi-layer component, or multi-phase component, as described in U.S. Pat. No. 5,928,572 entitled "Electrochromic Layer And Devices Comprising Same," U.S. Pat. No. 5,998,617 entitled "Electrochromic Compounds," U.S. Pat. No. 6,020,987 entitled "Electrochromic Medium Capable Of Producing A Pre-selected Color," U.S. Pat. No. 6,037,471 entitled "Electrochromic Compounds," U.S. Pat. No. 6,141,137 entitled "Electrochromic Media For Producing A Pre-selected Color," U.S. Pat. No. 6,193,912 entitled "Near Infrared-Absorbing Electrochromic Compounds And Devices Comprising Same," U.S. Pat. No. 6,249,369 entitled "Coupled Electrochromic Compounds With Photostable Dication Oxidation States," and U.S. Pat. No. 6,137,620 entitled "Electrochromic Media With Concentration Enhanced Stability, Process For The Preparation Thereof and Use In Electrochromic Devices," which are herein incorporated by reference in their entirety.

Referring now to FIGS. 3A-B, the electro-optic structure 114 includes a cathodic film 122 and an anodic film 126. The cathodic film 122 may have a thickness $T_{CA}$ and the anodic film 126 may have a thickness $T_{AN}$. As illustrated in FIGS. 3A-B, the cathodic film 122 is positioned, or otherwise disposed, on the first electrically conductive layer 82 and the anodic film 126 is positioned, or otherwise disposed, on the second electrically conductive layer 98. It will be understood by one having ordinary skill in the art that construction of the described disclosure and other components is not limited to any specific material. Other exemplary embodiments of the disclosure disclosed herein may be formed from a wide variety of materials, unless described otherwise herein. It will be understood that the locations of the cathodic film 122 and the anodic film 126 may be reversed without departing from the spirit and teachings of the disclosure. In electrochromic examples of the electro-optic structure 114, the cathodic film 122 contains the cathodic component and the anodic film 126 contains the anodic component.

The cathodic film 122 and the anodic film 126 may be in direct contact with one another, as illustrated in FIG. 3A, or may be separated by an electrolyte (e.g., a liquid, gel, or solid material containing a soluble salt that promotes ionic conductivity). In one aspect, as illustrated in FIG. 3B, the cathodic film 122 and anodic film 126 can be separated by an electrolyte layer 146. The electrolyte layer 146 may be a gel (e.g., a semi-liquid configured to provide a solvent and an electrolyte salt, which may permeate the cathodic and anodic films 122, 126) or polymeric electrolyte. In examples utilizing a polymeric or gel electrolyte as the electrolyte layer 146, the polymeric electrolyte may include poly(styrene-ran-ethylene), polystyrene-block-poly(ethylene-ran-butylene), poly(styrene-ran-ethylene), polystyrene-block-poly(ethylene/butylene)-block-polystyrene, poly(ethylene glycol), poly(methyl methacrylate), poly(2-hydroxyethyl-methacrylate-ran-methylacrylate), or other polymer gels disclosed in other polymer electrolytes and/or combinations thereof. Additional electrochromic gels and materials can be found in U.S. Pat. No. 6,268,950, issued Jul. 31, 2001 and entitled "Electrochromic Mirror with Two Thin Glass Elements and a Gelled Electrochromic Medium," and U.S. Pat. No. 7,001,540, issued Feb. 21, 2006 and entitled "Electrochromic Medium having a Self-healing Cross-linked Polymer Gel and Associated Electrochromic Device," both of which are hereby incorporated by reference in their entirety. The polymeric or gel electrolyte may additionally include a plasticizer that will help facilitate ion conductivity (e.g., propylene carbonate or gamma-butyrolactone) and a supporting electrolyte salt (e.g., tetraethylammonium tetrafluoroborate or tetraethylammonium hexafluorophosphate). The electrolyte layer 146 may partially permeate the cathodic and anodic films 122, 126.

According to an aspect of the present disclosure, the cathodic film 122 includes a first polymer matrix in which the cathodic component is sequestered by the first polymer matrix and the anodic film 126 includes a second polymer matrix in which the anodic component is sequestered by the second polymer matrix. As used herein, a component can be sequestered by a polymer matrix by confining the component within the polymer matrix to limit the component's movement and/or reactivity or by covalently bonding the component to the polymer matrix such that the component is attached to the polymer matrix. The cathodic component of the present disclosure can be confined within the first polymer matrix of the cathodic film 122 or covalently bonded to the first polymer matrix such that the cathodic component is attached to the first polymer matrix. The anodic component of the present disclosure can be confined within the second polymer matrix of the anodic film 126 or covalently bonded to the second polymer matrix such that the anodic component is attached to the second polymer matrix. The cathodic component and/or the anodic component can be bonded to the first and second polymer matrices, respectively, by functionalization of the cathodic and/or the anodic component. The first and second polymer matrices may be the same or different. According to an aspect of the disclosure, either or both of the cathodic and anodic components can be confined within and/or covalently bonded to the respective first and second polymer matrices.

Conventional solution-phase electro-optic elements typically contain at least one anodic (oxidizable) material, at least one cathodic (reducible) material, and a solvent. An electric potential can be applied to the conventional solution-phase electro-optic element to cause the element to transition between transparent and darkened states. Internal diffusion processes can result in the activated cathodic and anodic materials undergoing additional charge transfer processes that can result in continual self-erasing upon removal of the electric potential. Sequestering the cathodic and anodic components in a polymer matrix can decrease the occurrence of the additional charge transfer processes that can result in self-erasing upon removal of the electric potential.

Non-limiting examples of a suitable cathodic component according to the present disclosure includes a viologen, a low-dimerizing viologen, a non-dimerizing viologen, a di-acrylate viologen, a di-vinyl viologen, a di-vinyl ether viologen, a di-epoxy viologen, a di-oxetane viologen, a di-alcohol viologen, a ferrocenium, or derivatives thereof. In some aspects, the cathodic component can include: 2,7-bis-(vinyl-ether)-benzo(lmn)(3,8)phenanthroline-1,3,6,8-tetraone; 2,7-bis-(vinyl)-benzo(lmn)(3,8)phenanthroline-1,3,6,8-tetraone; 2,7-bis-(acrylate)-benzo(lmn)(3,8)phenanthroline-1,3,6,8-tetraone; 2,7-bis-(methacrylate)-benzo(lmn)(3,8)phenanthroline-1,3,6,8-tetraone; 2,7-bis-(epoxy)-benzo(lmn)(3,8)phenanthroline-1,3,6,8-tetraone; 2,7-bis-(oxetane)-benzo(lmn)(3,8)phenanthroline-1,3,6,8-tetraone; 2,7-bis-(hydroxy)-benzo(lmn)(3,8)phenanthroline-1,3,6,8-tetraone; 2,9-bis(vinyl ether)-anthra[2,1,9-def:6,5,10-d'e'f']diisoquinoline; 1,3,8,10-tetraone, 2,9-bis(vinyl)-anthra[2,1,9-def:6,5,10-d'e'f']diisoquinoline; 1,3,8,10-tetraone, 2,9-bis(acrylate)-anthra[2,1,9-def:6,5,10-d'e'f']diisoquinoline; 1,3,8,10-tetraone, 2,9-bis(epoxy)-anthra[2,1,9-def:6,5,10-d'e'f']diisoquinoline; 1,3,8,10-tetraone, 2,9-bis(oxetane)-anthra[2,1,9-def:6,5,10-d'e'f']diisoquinoline; 1,3,8,10-tetraone, 2,9-bis(methacrylate)-anthra[2,1,9-def:6,5,10-d'e'f']diisoquinoline; 1,3,8,10-tetraone, 2,9-bis(hydroxy)-anthra[2,1,9-def:6,5,10-d'e'f']diisoquinoline, or a combination of any of the cathodic components described herein.

The cathodic component can be covalently attached to, or confined within, the first polymer matrix. The first polymer matrix can be configured to prevent or minimize substantial diffusion of the cathodic component. The cathodic component may be sequestered within the polymer matrix by being physically trapped within, or the cathodic material may be functionalized such that it is amenable to being polymerized or reacted with the polymer to be covalently bonded to the polymer.

Non-limiting examples of a suitable anodic component according to the present disclosure include a phenoxazine, a phenazine, a phenothiazine, a triphenodithiazine, a carbazole, a indolocarbazole, a biscarbazole, a ferrocene or derivatives thereof, covalently attached to, or confined within, the second polymer matrix, the second polymer matrix configured to prevent or minimize substantial diffusion of the anodic component. As with the cathodic component, the anodic component may be sequestered within the polymer matrix by being physically trapped within, or the anodic component may be functionalized such that it is amenable to being polymerized or reacted with the polymer to be covalently bonded to the polymer. In one aspect, the anodic component can be selected from: a phenoxazine; a phenoxazine derivative; a phenazine; a phenazine derivative; a phenothiazine; a phenothiazine derivative; a triphenodithiazine; a triphenodithiazine derivative; a carbazole; a carbazole derivative; an indolocarbazole; an indolocarbazole derivative; a biscarbazole; a biscarbazole derivative; a ferrocene; a ferrocene derivative; 5, 10-di-(vinyl-ether)-5, 10-dihydrophenazine; 5, 10-di-(vinyl)-5,10-dihydrophenazine; 5, 10-di-(acrylate)-5,10-dihydrophenazine; 5,10-di-(methacrylate)-5,10-dihydrophenazine; 5, 10-di-(epoxy)-5,10-dihydrophenazine; 5, 10-di-(oxetane)-5,10-dihydrophenazine; 5,10-di-(alcohol)-5,10-dihydrophenazine; 5, 10-dimethyl-5,10-dihydrophenazine-2, 7-di-(vinyl ether); 5, 10-dimethyl-5,10-dihydrophenazine-2, 7-di-(vinyl); 5, 10-dimethyl-5,10-dihydrophenazine-2, 7-di-(acrylate); 5,10-dimethyl-5,10-dihydrophenazine-2,7-di-(methacrylate); 5, 10-dimethyl-5, 10-dihydrophenazine-2, 7-di-(epoxy); 5, 10-dimethyl-5,10-dihydrophenazine-2, 7-di-(oxetane); 5,10-dimethyl-5,10-dihydrophenazine-2,7-di-(alcohol); 7,14-dimethyl-7,14-dihydrobenzo[5,6][1,4]thiazino[2,3-b]phenothiazine-3,10-di-(vinyl ether); 7,14-dimethyl-7,14-dihydrobenzo[5,6][1,4]thiazino[2,3-b]phenothiazine-3,10-di-(vinyl); 7,14-dimethyl-7,14-dihydrobenzo[5,6][1,4]thiazino[2,3-b]phenothiazine-3,10-di-(acrylate); 7,14-dimethyl-7,14-dihydrobenzo[5,6][1,4]thiazino[2,3-b]phenothiazine-3,10-di-(methacrylate); 7,14-dimethyl-7,14-dihydrobenzo[5,6][1,4]thiazino[2,3-b]phenothiazine-3,10-di-(epoxy); 7,14-dimethyl-7,14-dihydrobenzo[5,6][1,4]thiazino[2,3-b]phenothiazine-3,10-di-(oxetane); 7,14-dimethyl-7,14-dihydrobenzo[5,6][1,4]thiazino[2,3-b]phenothiazine-3,10-di-(dihydroxy), or a combination thereof.

The cathodic or anodic components are sequestered within a polymer matrix, which may be a solid polymer or a gel polymer (i.e., a polymer swollen with a solvent). For example, the polymer may be an acrylate-based polymer that is dissolved in a solvent which incorporates the anodic or cathodic component. This solution is then coated on the conductive surface of a substrate, followed by removal of the solvent. The resultant film is an acrylate film that may be hard or tacky to the touch. In another example, the polymer film may be a gel that contains solvent as well as the anodic or cathode component. Optionally, the polymer film may be subsequently cross-linked for increased mechanical stability. Other non-limiting examples of polymer matrix systems that could be used to sequester an anodic and/or cathodic component include: polyacrylate, polymethacrylates, polyethers, polyesters, polycarbonates, polyurethanes, polysiloxanes, polysilanes, polyacrylonitriles, polystyrenes, polymethacrylonitriles, polyamides, polyimides, polyvinylidene halides, and co-polymers, or combinations of any two or more thereof. Further examples of polymer matrix materials used in electrochromic devices can be found in U.S. Pat. Nos. 6,635,194; 5,940,201; 5,928,572; and 9,964,828, which are herein incorporated by reference in their entirety.

According to another aspect of the disclosure, the anodic and/or cathodic components may also be part of the polymer matrix with the anodic and/or cathodic component being covalently bound to the polymer. This may be accomplished with the presence of a functional group on the anodic and/or cathodic component that is reacted with the polymer or monomers that form the polymer of the film. In one aspect, the anodic component and/or the cathodic component are incorporated into a compound that includes one or more functional groups that are capable of reacting with the polymer and/or monomers to form the respective anodic and cathodic film. In one example, the anodic component and/or the cathodic component are incorporated into a compound that includes one or more polymerizable functional groups that are capable of reacting with a component of the polymer matrix (e.g., the polymers or monomers forming the matrix) to form the respective anodic and cathodic film. In this manner, the anodic and/or cathodic component may be covalently bonded to the respective polymer matrix by one or more linkages. For example, where the anodic or cathodic components contain a hydroxyl group, the anodic or cathodic component may be bound into a polymer matrix via a condensation reaction or react with an isocyanate functionality to form a polyurethane-based polymer matrix. Amines may also react with isocyanate functionalities to form urea and biuret linkages. It is also within the scope of the present disclosure to utilize other cross-linked polymer matrix systems that can be formed using a multi-functional epoxy in combination with a curing agent like an amine, alcohol, or anhydride or through base or acid catalyzed homo- or co-polymerization.

Non-limiting examples of materials that may be used as the first and/or second polymer matrix materials for covalently bonding with the cathodic and/or the anodic components include: polymethylmethacrylate, polypropylene methacrylate, polystyrene, polyurethanes, polyethers, polyesters, polycarbonates, polysiloxanes, polysilanes, polyacrylonitriles, polymethacrylonitriles, polyamides, polyimides, polyvinylidene halides, and co-polymer and combinations of thereof. Further examples of polymer matrix materials can be found in U.S. Pat. Nos. 6,635,194; 5,940,201; 5,928,572; and 9,964,828, which are herein incorporated by reference in their entirety.

According to an aspect of the present disclosure, the cathodic and anodic films 122 and 126 can be prepared utilizing any suitable method for providing a film having the desired thickness and uniformity. For example, the cathodic and anodic films 122 and 126 can be prepared using a Mayer or other rod coating process or a doctor blade draw-down process or applied as a spray coating or by screen-printing or by a slot-die coating In some aspects, the electro-optic element may include an electrolyte, which may be in the form of a solvent and a salt. The salt may be a metal salt or an ammonium salt. Non-limiting examples of suitable solvents for use in the electrolyte include: 3-methylsulfolane, dimethyl sulfoxide, dimethyl formamide, tetraglyme, and other polyethers; alcohols such as ethoxyethanol; nitriles, such as acetonitrile, glutaronitrile, 3-hydroxypropionitrile, and 2-methylglutaronitrile; ketones including 2-acetylbutyrolactone, and cyclopentanone; cyclic esters including beta-propiolactone, gamma-butyrolactone, and gamma-valerolactone; propylene carbonate (PC), ethylene carbonate; and homogenous mixtures thereof. Non-limiting examples of suitable salts include: metal or ammonium salts, such as $Li^+$, $Na^+$, $K^+$, $NR'_4{}^+$ (where each R' is individually H, alkyl, or cycloalkyl) of the following anions $F^-$, $Cl^-$, $Br^-$, $I^-$, $BF_4{}^-$, $PF_6{}^-$, $SbF_6{}^-$, $AsF_6{}^-$, $ClO_4{}^-$, $SO_3CF_3{}^-$, $N(CF_3SO_2)_2{}^-$, $C(CF_3SO_2)_3{}^-$, $N(SO_2C_2F_5)_2{}^-$, $Al(OC(CF_3)_3)_4{}^-$, or $BAr_4{}^-$, wherein Ar is an aryl or fluorinated aryl group such as, but not limited to, $C_6H_5$, $3,5\text{-}(CF_3)_2C_6H_3$, or $C_6F_5$.

With regard to the substrates and conductive coatings on the substrates, those typically used in solution-based electrochromic devices may be used. According to an aspect of the present disclosure, the first and/or second substrates 70, 86 may be glass, metal, plastic, or ceramic. The electrically conductive coatings 82, 98 on one or more of the first and second substrates 70, 86 may be transparent or opaque depending upon the intended use of the electrochromic device incorporating the electro-optic element. For example, where the device is a window, both electrically conductive coatings 82, 98 should be substantially transparent, and where the device is a mirror at least one of the electrically conductive coatings 82, 98 is transparent.

Non-limiting examples of transparent electrically conductive materials include: fluorine doped tin oxide (FTO), indium tin oxide (ITO), doped zinc oxide, indium zinc oxide, metal oxide/metal/metal oxide, silver nano-wire coatings, carbon nanotubes, graphene coatings, wire grids, and conductive polymers such as, but not limited to, poly(3,4-ethylenedioxythiophene) (PEDOT). Non-limiting examples of non-transparent electrically conductive coatings include metal coatings such as rhodium, chromium, nickel, silver, gold, and other metals, or mixtures of any two or more thereof.

Aspects of the present disclosure relate to providing the cathodic and anodic films 122 and 126 such that one of the cathodic component or the anodic component is present in excess relative to the other. According to one aspect, providing the cathodic or anodic component in excess relative to the other is based on a relative thickness of the cathodic and anodic films 122, 126. In examples in which a charge capacity or a concentration per unit film area of the cathodic and anodic films 122, 126 are substantially equal, the thickness $T_{CA}$ of the cathodic film 122 can be greater than the thickness $T_{AN}$ of the anodic film 126 to provide the cathodic component in excess relative to the anodic component. Alternatively, to provide the anodic component in excess relative to the cathodic component, the thickness $T_{AN}$ of the anodic film 126 can be greater than the thickness $T_{CA}$ of the cathodic film 122.

In another aspect, providing the cathodic or anodic component in excess relative to the other can be based on a relative molar amount of each of the cathodic component and the anodic component. For example, the cathodic film 122 can be configured such that a molar amount of the cathodic component is greater than a molar amount of the anodic component in the anodic film 126. In some aspects, a ratio of a molar amount of the cathodic component in the cathodic film 122 to a molar amount of the anodic component in the anodic film 126 is greater than 1. In another aspect, a ratio of a molar amount of the cathodic component in the cathodic film 122 to a molar amount of the anodic component in the anodic film 126 is from about 1.01:1 to about 5:1, about 1.01:1 to about 4:1, about 1.01:1 to about 3:1, about 1.01:1 to about 2:1, about 1.1:1 to about 5:1, about 1.1:1 to about 4:1, about 1.1:1 to about 3:1, about 1.1:1 to about 2:1, about 1.5:1 to about 5:1, about 2:1 to about 5:1, about 3:1 to about 5:1, about 4:1 to about 5:1, about 1.25:1 to about 5:1, about 1.25:1 to about 4:1, about 1.25:1 to about 3:1, about 1.25:1 to about 2:1, about 1.5:1 to about 2:1, about 1.5:1 to about 3:1, or about 1.5:1 to about 4:1. In some aspects, a ratio of a molar amount of the cathodic component in the cathodic film 122 to a molar amount of the anodic component in the anodic film 126 is about 1.01:1, about 1.1:1, about 1.25:1, about 1.5:1, about 2:1, about 3:1, about 4:1, or about 5:1. Alternatively, the anodic film 126 can be configured such that a molar amount of the anodic component is greater than a molar amount of the cathodic component in the cathodic film 122.

In one aspect, the relative molar amounts of the cathodic and anodic components is related to a relative thickness of the respective cathodic and anodic films 122, 126. In another aspect, the relative molar amounts of the cathodic and anodic components is related to a relative charge capacity of the cathodic and anodic films 122, 126, respectively. For some materials, the thickness of the film may be directly proportional to the charge capacity and thus adjusting the relative charge capacities of the film (i.e., the relative molar amounts of the electroactive components) can be practically achieved by adjusting the thickness of the film. According to an aspect of the present disclosure, one of the cathodic or the anodic component can be configured to exhibit an increased charge capacity relative to the other by from about 1% to about 60%, about 1% to about 50%, about 1% to about 40%, about 1% to about 20%, about 1% to about 10%, about 1% to about 5%, about 5% to about 60%, about 5% to about 50%, about 5% to about 40%, about 5% to about 30%, about 10% to about 60%, about 10% to about 50%, about 10% to about 40%, about 10% to about 30%, about 15% to about 60%, about 15% to about 50%, about 15% to about 40%, about 15% to about 30%, about 20% to about 60%, about 20% to about 50%, about 20% to about 40%, about 20% to about 30%, about 30% to about 60%, about 30% to about 50%, about 30% to about 40%, about 40% to about 60%, about 40% to about 50%, about 50% to about 60%, about 1% to about 25%, about 5% to about 25%, about 10% to about 25%, about 15% to about 25%, about 20% to about 25%, about 5% to about 20%, about 10% to about 20%, about 15% to about 20%, about 5% to 15%, about 10% to about 15%, or about 5% to about 10%.

In another aspect, the relative molar amounts of the cathodic and anodic components relates to a percent loading of the cathodic and anodic components in their respective cathodic and anodic films 122, 126. In one aspect, the cathodic and anodic films 122, 126 can be configured such that a molar amount of the electroactive component per unit film area in one of the cathodic and anodic films 122, 126 is greater than the other. For example, an amount of the cathodic component confined within a unit film area of the cathodic film 122 can be greater than an amount of the anodic component confined within a unit film area of the anodic film 126. In another example, an amount of the anodic material confined within a unit film area of the anodic film 126 is greater than an amount of the cathodic component confined within a unit film area of the cathodic film 122. In another example, the relative amounts of cathodic and anodic material per unit film area may be based on the structure of the functional groups used to cross-link the electroactive material with the polymer matrix forming the film such that the polymeric structure of one of the films contains a higher loading of the cathodic or anodic component in the polymeric structure. In some examples, one or both of the cathodic and anodic films 122, 126 may swell or expand more than the other due to solvent uptake. The molar amounts of the cathodic and anodic components in each respective cathodic and anodic films 122, 126 can be selected such that the desired excess of one component is maintained, taking into consideration possible swelling of the film. In one aspect, the relative amounts of the cathodic and anodic components are based on a parameter that is not affected by changes in film volume or dimensions, such as may be due to swelling, an example of which includes a molar amount of each component carried by the respective film.

According to one aspect of the present disclosure, either the cathodic component or the anodic component is provided in excess in order to limit the formation of a particular oxidation state of one of the cathodic or anodic components. Without being bound by theory, the reduction-oxidation reactions that occur in an exemplary electro-optic element when an electric potential is applied can generally be represented by the following Equations 1 and 2:

$$AN^0 \leftrightarrow AN^+ \leftrightarrow AN^{2+} \quad \text{(Equation 1)}$$

$$CA^0 \leftrightarrow CA^- \leftrightarrow CA^{2-} \quad \text{(Equation 2)}$$

wherein "AN" represents the anodic component and "CA" represents the cathodic component. In the exemplary electro-optic element, the components $AN^0$ and $CA^0$ in Equations 1 and 2 are representative of the electroactive species responsible for the transparent state of the electro-optic element when an electric potential has not been applied. When a sufficient electric potential is applied, the anodic component $AN^0$ is oxidized to a first oxidation state, a first oxidized state $AN^+$, while the cathodic component $CA^0$ is reduced to a first oxidation state, a first reduced state $CA^-$, which results in the electro-optic element transitioning from the transparent state to the darkened state.

In some scenarios, either or both the anodic component and the cathodic component may include second (or additional) oxidation states, for example $AN^{2+}$ and $CA^{2-}$. For example, the anodic component may be oxidized to a second oxidation state, a second or doubly oxidized state $AN^{2+}$ (Equation 1) and/or the cathodic component may be reduced to a second oxidation state, a second or doubly reduced state $CA^{2-}$ (Equation 2). Either or both of the second oxidation states for the anodic and/or the cathodic material may represent a state that is less stable than the respective first electrochemically activated state.

In operation, the electrochromic device is operated at a potential difference that favors formation of the singly oxidized species $AN^+$ and singly reduced species $CA^-$, while trying to minimize formation of the doubly oxidized species $AN^{2+}$ and doubly reduced species $CA^{2-}$. However, a small proportion of either or both the $AN^+$ and $CA^-$ may undergo an additional process, referred to as disproportionation, to form the second oxidation states. These second oxidation states are typically less stable and can often result in irreversible chemical change, resulting in decomposition or reaction of the cathodic and/or anodic component over time, which can affect the lifetime of the electrochromic device incorporating such films.

According to an aspect of the present disclosure, the cathodic and anodic films 122 and 126 are configured such that one of the cathodic component or the anodic component is present in excess relative to the other in order to limit formation of a second oxidation state of the electroactive component in molar excess. In one aspect, when the second oxidation state of the cathodic component is less stable compared to the second oxidation state of the anodic component, the cathodic and anodic films 122 and 126 can be configured to provide the cathodic component in excess such that the reduction-oxidation reactions are limited by the amount of the anodic component available to react, thus limiting formation of the less stable cathodic second oxidation state. In another aspect, when the second oxidation state of the cathodic component produces an irreversible chemical change, the cathodic and anodic films 122 and 126 can be configured to provide the cathodic component in excess such that the reduction-oxidation reactions are limited by the amount of the anodic component available to react, thus limiting formation of the cathodic second oxidation state. Conversely, when the anodic component includes a less stable second oxidation state or an oxidation state that reacts to produce an irreversible chemical change, the cathodic and anodic films 122 and 126 can be configured to provide the anodic component in excess in order to limit formation of the anodic second oxidation state.

While the present disclosure is discussed in the context of first and second oxidation states (oxidation state n and oxidation state n+1), aspects of the present disclosure are also applicable in configurations in which the primary, desired oxidation state for either or both the anodic and cathodic components is a second (or additional) oxidation state (n+2, n+3, n+4, etc. . . . ) and the undesired oxidation state is one or more additional oxidation states.

The following examples describe various features and advantages provided by the present disclosure, and are in no way intended to limit the present disclosure and the appended claims.

EXAMPLES

Example 1

Exemplary electro-optic elements according to the present disclosure (Exemplary Samples 1-6) and Comparative electro-optic elements (Comparative Samples 1-2) were prepared and the coloring performance was tested as described below. The Exemplary Samples 1-6 and Comparative Samples 1-2 were prepared using the same cathodic and anodic components, however, the film thickness and charge capacity was varied for each of the test samples, as listed in Table 1 below.

Both the Exemplary and Comparative samples were prepared using 3"×3" square pieces of 2.2 mm thick glass as the first and second substrates. A 0.15 micrometer ITO layer was applied to both glass substrates to form an electrically conductive layer on each glass substrate. One of the ITO-coated glass substrates was coated with a cathodic film including a cathodic component and the other ITO-coated glass substrate was coated with an anodic film including an anodic component.

Figure 4A:
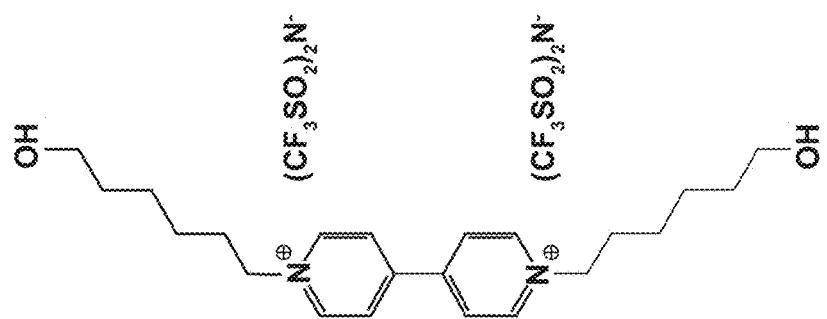
FIG. 4A illustrates the chemical structure of a cathodic component, according to an aspect of the present disclosure.

The cathodic film was prepared by combining the cathodic component of FIG. 4A, a multi-functional isocyanate, a solvent, and a catalyst. The cathodic component of FIG. 4A (referred to as "$VC_6NTF$") is a viologen-based material including two $C_6$ alkyl alcohol functional groups which react with the isocyanate to form a cross-linked film. The film was deposited on one of the ITO-coated glass substrates using the Mayer rod method. The deposited cathodic film was cured overnight at 60° C. under nitrogen until gelled. The amount of deposited cathodic component was varied to provide samples having different film thickness/charge capacities, as identified in Table 1 below.

Figure 5B:
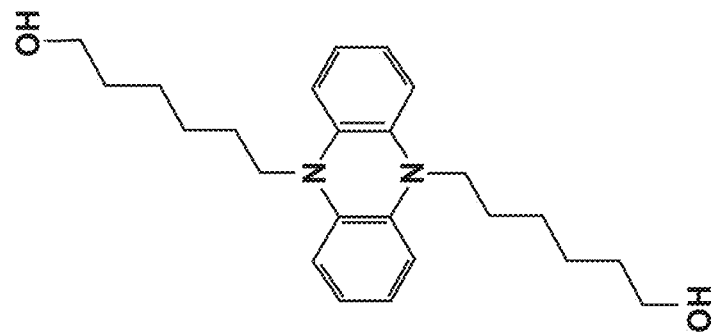
FIG. 5B illustrates the chemical structure of an anodic component, according to an aspect of the present disclosure.
Figure 5A:
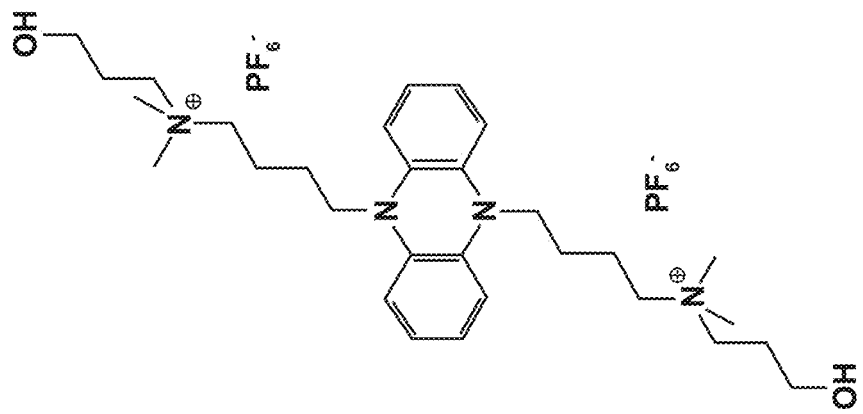
FIG. 5A illustrates the chemical structure of an anodic component, according to an aspect of the present disclosure.

The anodic film was prepared by combining the anodic component of FIG. 5A, an isocyanate, a solvent, and a catalyst. The anodic component of FIG. 5A (referred to as "$PhC_4NC_3PF_6$") is a phenazine-based material that includes two hydroxy amine functional groups ($C_4NC_3$) which react with the isocyanate to form a cross-linked film. The film was deposited on one of the ITO-coated glass substrates using the Mayer rod method. The deposited anodic film was cured overnight at 60° C. under nitrogen until gelled. The amount of deposited anodic component was varied to provide samples having different film thickness/charge capacities, as identified in Table 1 below.

The glass substrates were positioned with their respective cathodic and anodic films in a spaced-apart relationship facing each other and an epoxy seal was placed around the perimeter of the glass substrates. The epoxy seal was cured under an inert atmosphere to form an electro-optic cell, leaving offsets for attachment of electrical contacts. The distance between the two glass substrates was about 600 micrometers with the electrolyte layer containing a solvent, gel components, electrolyte salt, and catalyst. 100 millimolar (mM) tetraethylammonium tetrafluoroborate ($TEABF_4$) was used as the electrolyte salt.

Table 1 identifies the characteristics of the cathodic and anodic components for each of the Exemplary Samples 1-6 and Comparative Samples 1-2.

TABLE 1

Exemplary & Comparative Electro-Optic Samples.

| Sample | Cathodic Film Thickness (nm) | Cathodic Film Charge Capacity (mC/cm$^2$) | Anodic Film Thickness (nm) | Anodic Film Charge Capacity (mC/cm$^2$) | Excess Component |
|---|---|---|---|---|---|
| Exemplary Sample 1 | 908 | 10.1 | 554 | 5.5 | Cathodic |
| Exemplary Sample 2 | 885 | 9.9 | 570 | 5.6 | Cathodic |
| Exemplary Sample 3 | 1694 | 18.3 | 985 | 9.7 | Cathodic |
| Exemplary Sample 4 | 1782 | 19.2 | 1035 | 10.2 | Cathodic |
| Exemplary Sample 5 | 3613 | 38.3 | 558 | 5.5 | Cathodic |
| Exemplary Sample 6 | 2141 | 22.9 | 620 | 6.1 | Cathodic |
| Comparative Sample 1 | 879 | 9.8 | 1294 | 12.8 | Anodic |
| Comparative Sample 2 | 846 | 9.5 | 1331 | 13.1 | Anodic |

Figure 6:
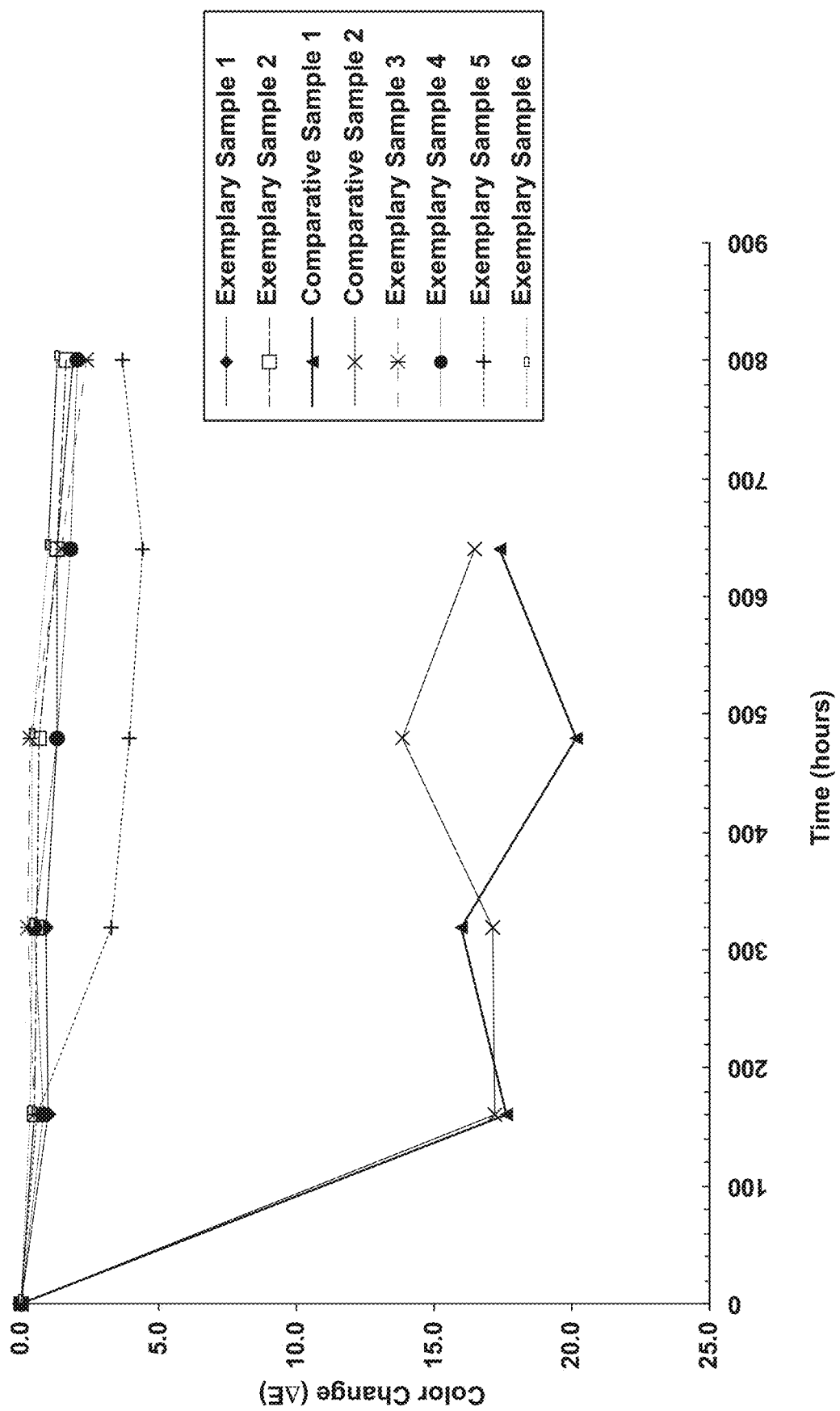
FIG. 6 is a plot of color change as a function of time for Exemplary and Comparative electro-optic elements, according to an aspect of the present disclosure.

FIG. 6 illustrates the change in color of Exemplary Samples 1-6 and Comparative Samples 1-2 under thermal testing. The Exemplary Samples 1-6 and Comparative Samples 1-2 of Table 1 were evaluated by measuring the change in color of an un-powered sample after cycling at elevated temperatures for 800 hours. The samples were placed in an oven held at 70° C. and connected to a programmable external power supply that cycled the samples on for 5 minutes at 0.8 V and shorted for 5 minutes. CIELAB color space measurements were performed weekly using an X-rite SP62 spectrophotometer after allowing the parts to cool to room temperature. The spectral data was captured at 5 nm increments from 360 nm to 830 nm.

As demonstrated in FIG. 6, the Exemplary Samples 1-6 in which the cathodic component was in excess relative to the anodic component all experienced significantly less change in color of the un-powered device over time compared to the Comparative Samples 1-2 in which the anodic component was in excess. When power is supplied to the sample, the cathodic component $VC_6NTF$ is reduced and the anodic component $PhC_4NC_3PF_6$ is oxidized (as described above with respect to Equations 1 and 2), resulting in the electro-optic cell transitioning from a transparent state to a colored state. When power is removed from the sample and shorted, the electro-optic cell returns to the transparent state, referred to as clearing. The cathodic component $VC_6NTF$ can also undergo a second reduction to a second oxidation state that is less stable than the first oxidation state. The anodic component $PhC_4NC_3PF_6$ can also be oxidized a second time to a second oxidation state that is less stable than the first oxidation state. Overtime, the second reduction and oxidation reactions can inhibit the ability of the sample to return to the transparent state and thus the color of the unpowered device can increase over time, as demonstrated by the increase in color change ($\Delta E$) in FIG. 6 (i.e., increase in $\Delta E$ values).

FIG. 6 demonstrates that providing the cathodic component $VC_6NTF$ in excess relative to the anodic component $PhC_4NC_3PF_6$s Substantially decreases the color change ($\Delta E$) of the samples over time, which may result in an increase in the lifetime of electrochromic devices incorporating these electro-optic cells. Providing the cathodic component $VC_6NTF$ in excess compared to the anodic component $PhC_4NC_3PF_6$ limits the likelihood of the second reduction of the cathodic component $VC_6NTF$ due to the limited availability of the anodic component $PhC_4NC_3PF_6$. While not intending to be limited by any theory, it is believed that the second oxidation state of the cathodic component $VC_6NTF$ is less stable than the second oxidation state of the anodic component $PhC_4NC_3PF_6$ under the conditions of this test and this is why a significant improvement in the color change of the devices is seen for the Exemplary Samples 1-6 when the cathodic component is in excess compared to when the anodic component is provided in excess (Comparative Samples 1-2).

Example 2

Exemplary electro-optic elements according to the present disclosure (Exemplary Samples 7-10) and Comparative electro-optic elements (Comparative Samples 3-4) were prepared and the coloring performance was tested as described below. Exemplary Samples 7-10 and Comparative Samples 3-4 were prepared in a manner similar to that described above for Example 1, however, a different anodic monomer was used in forming the anodic film. The Exemplary Samples 7-10 and Comparative Samples 3-4 were prepared using the same cathodic and anodic components, however, the film thickness and charge capacity was varied for each of the test samples, as listed in Table 2 below.

Both the Exemplary and Comparative samples were prepared using 3"×3" square pieces of 2.2 mm thick glass as the first and second substrates. A 0.15 micrometer ITO layer was applied to both glass substrates to form an electrically conductive layer on each glass substrate. One of the ITO-coated glass substrates was coated with a cathodic film including a cathodic component and the other ITO-coated glass substrate was coated with an anodic film including an anodic component.

The cathodic film was prepared by combining the cathodic component of FIG. 4A, a multi-functional isocyanate, a solvent, and a catalyst. The cathodic component of FIG. 4A (referred to as "VC$_6$NTF") is a viologen-based material including two C$_6$ alkyl alcohol functional groups which react with the isocyanate to form a cross-linked film. The film was deposited on one of the ITO-coated glass substrates using the Mayer rod method. The deposited cathodic film was cured overnight at 60° C. under nitrogen until gelled. The amount of deposited cathodic component was varied to provide samples having different film thickness/charge capacities, as identified in Table 2 below.

The anodic film was prepared by combining the anodic component of FIG. 5B, a multi-functional isocyanate, a solvent, and a catalyst. The anodic component of FIG. 5B (referred to as "PhC$_6$") is a phenazine-based material that includes two C$_6$ alkyl alcohol functional groups which react with the isocyanate to form a cross-linked film. The film was deposited on one of the ITO-coated glass substrates using the Mayer rod method. The deposited anodic film was cured overnight at 60° C. under nitrogen until gelled. The amount of deposited anodic component was varied to provide samples having different film thickness/charge capacities, as identified in Table 2 below.

The glass substrates were positioned with their respective cathodic and anodic films in a spaced-apart relationship facing each other and an epoxy seal was placed around the perimeter of the glass substrates. The epoxy seal was cured under an inert atmosphere to form an electro-optic cell, leaving offsets for attachment of electrical contacts. The distance between the two glass substrates was about 135 micrometers with the electrolyte layer containing solvent, gel components, electrolyte, and catalyst. 100 millimolar (mM) tetraethylammonium tetrafluoroborate (TEABF$_4$) was used as the electrolyte. The electrolyte layer was allowed to gel overnight before testing.

Table 2 identifies the characteristics of the cathodic and anodic components for each of the Exemplary Samples 7-10 and Comparative Samples 3-4.

TABLE 2

Exemplary & Comparative Electro-Optic Samples.

| Sample | Cathodic Film Thickness (nm) | Cathodic Film Charge Capacity (mC/cm$^2$) | Anodic Film Thickness (nm) | Anodic Film Charge Capacity (mC/cm$^2$) | Excess Component |
|---|---|---|---|---|---|
| Exemplary Sample 7 | 1662 | 18.0 | 710 | 9.6 | Cathodic |
| Exemplary Sample 8 | 1562 | 16.9 | 704 | 9.5 | Cathodic |
| Exemplary Sample 9 | 2115 | 22.7 | 1032 | 14.5 | Cathodic |
| Exemplary Sample 10 | 2102 | 22.5 | 947 | 13.2 | Cathodic |
| Comparative Sample 3 | 951 | 10.6 | 1030 | 14.4 | Anodic |
| Comparative Sample 4 | 971 | 10.8 | 1018 | 14.2 | Anodic |

Figure 7:
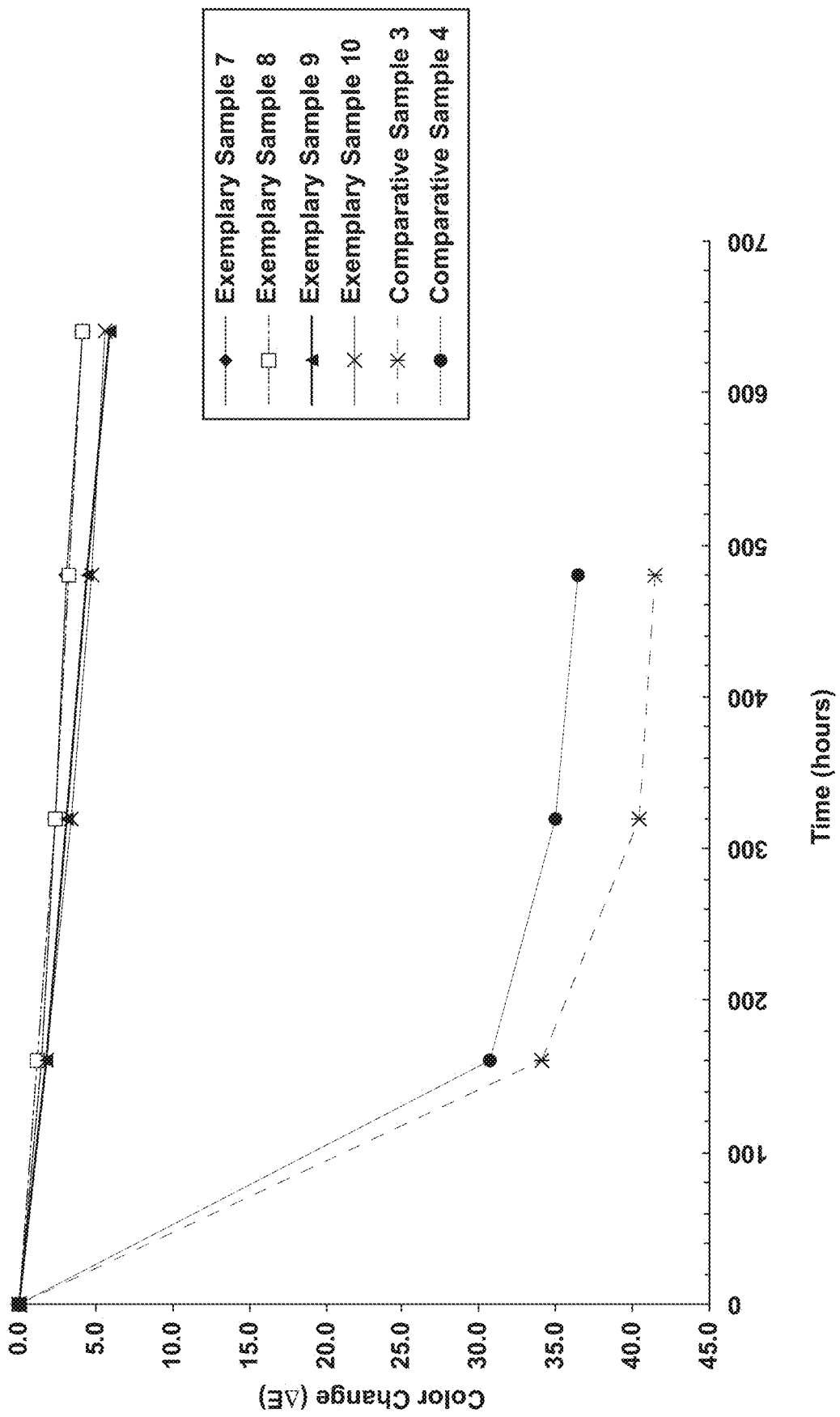
FIG. 7 is a plot of color change as a function of time for Exemplary and Comparative electro-optic elements, according to an aspect of the present disclosure.

FIG. 7 illustrates the change in color of Exemplary Samples 7-10 and Comparative Samples 3-4 under thermal testing. The Exemplary Samples 7-10 and Comparative Samples 3-4 of Table 2 were evaluated by measuring the change in color of an un-powered sample after cycling at elevated temperatures for 800 hours. The samples were placed in an oven held at 70° C. and connected to a programmable external power supply that cycled the samples on for 5 minutes at 0.8 V and shorted for 5 minutes. CIELAB color space measurements were performed weekly using an X-rite SP62 spectrophotometer after allowing the parts to cool to room temperature. The spectral data was captured at 5 nm increments from 360 nm to 830 nm.

As demonstrated in FIG. 7, the Exemplary Samples 7-10 in which the cathodic component was in excess relative to the anodic component all experienced significantly less change in color of the un-powered device over time compared to the Comparative Samples 3-4 in which the anodic component was in excess. When power is supplied to the sample, the cathodic component VC$_6$NTF is reduced and the anodic component PhC$_6$ is oxidized (as described above with respect to Equations 1 and 2), resulting in the electro-optic cell transitioning from a transparent state to a colored state. When the sample is shorted, the electro-optic cell returns to the transparent state, referred to as clearing. The cathodic component VC$_6$NTF can also undergo a second reduction to a second oxidation state that is less stable than the first oxidation state. The anodic component PhC$_6$ can also be oxidized a second time to a second oxidation state that is less stable than the first oxidation state. Overtime, the second reduction and oxidation reactions can inhibit the ability of the sample to return to the transparent state and thus the color of the unpowered device may increase over time, as demonstrated by the increase in color change (ΔE) in FIG. 7.

FIG. 7 demonstrates that providing the cathodic component VC$_6$NTF in excess relative to the anodic component PhC$_6$ substantially decreases the color change (ΔE) of the Exemplary Samples 7-10 over time compared to the Comparative Samples 3 and 4. The decrease in color change over time of the Exemplary Samples 7-10 may result in an increase in the lifetime of electrochromic devices incorporating these electro-optic cells compared to the Comparative Samples 3-4. Providing the cathodic component $VC_6NTF$ in excess compared to the anodic component $PhC_6$ limits the likelihood of the second reduction of the cathodic component $VC_6NTF$ due to the limited availability of the anodic component $PhC_6$. While not intending to be limited by any theory, it is believed that the second oxidation state of the cathodic component $VC_6NTF$ is less stable than the second oxidation state of the anodic component $PhC_6$ and this is why a significant improvement in the color change of the devices (i.e., less change in $\Delta E$ values) is seen for the Exemplary Samples 7-10 in which the cathodic component is in excess compared to Comparative Samples 3-4 in which the anodic component is provided in excess.

Example 3

Figure 8:
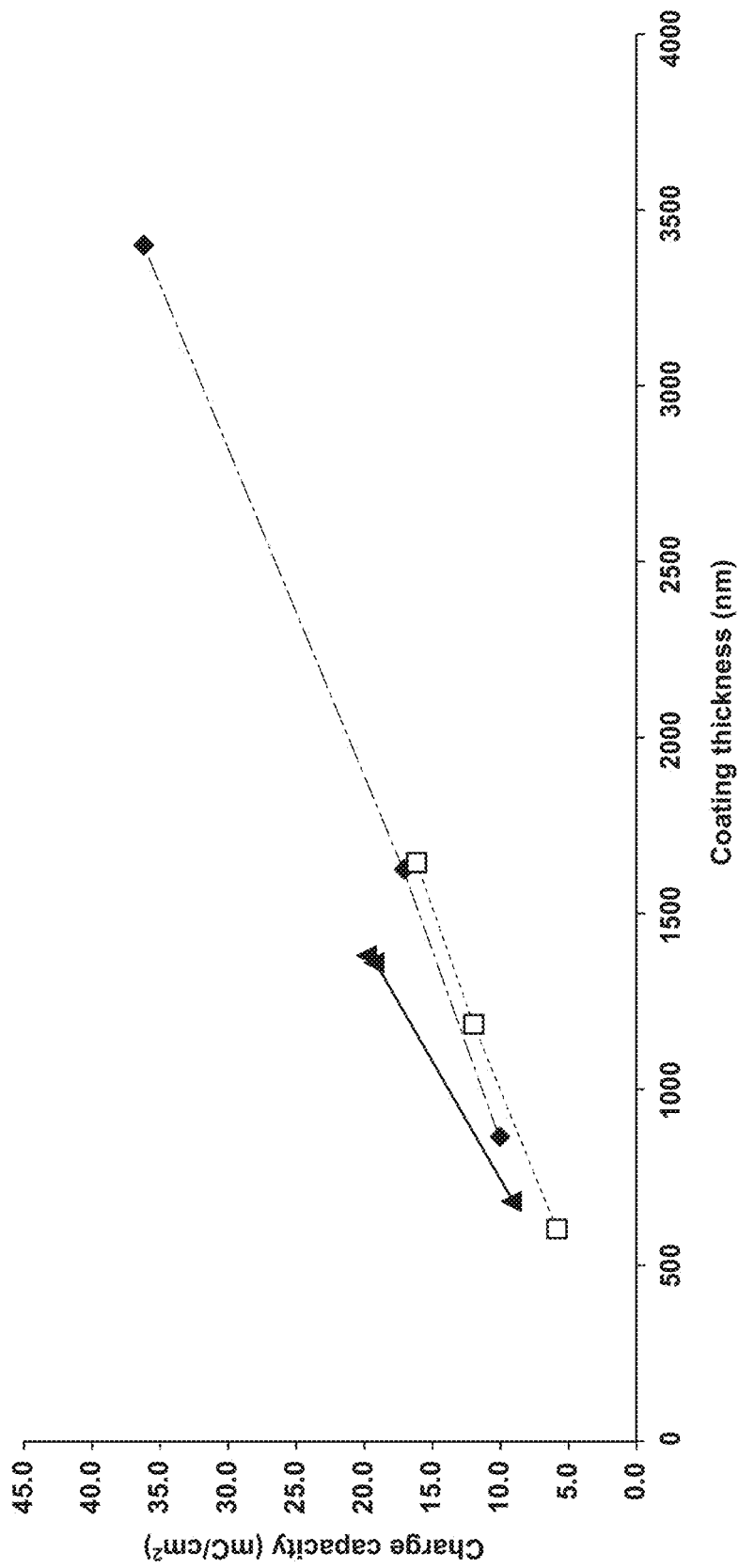
FIG. 8 is a plot of coating thickness as a function of charge capacity, according to an aspect of the present disclosure.

FIG. 8 illustrates the charge capacity as a function of film thickness for the cathodic and anodic films of Examples 1 and 2. Specifically, the charge capacity of the cathodic component $VC_6NTF$ (diamonds), anodic component $PhC_4NC_3PF_6$ (squares), and anodic component $PhC_6$ (triangles) is illustrated as a function of film thickness (data points are connected by lines for clarity and do not represent a linear regression fit). The data for each component was fit using a linear least squares regression model (not shown). The data in FIG. 8 demonstrates that these films exhibit a linear relationship between the charge capacity of the film and film thickness, as demonstrated by an $R^2$ value of greater than 0.99 for the linear least squares regression model.

The data in FIG. 8 can be used to determine the relative thicknesses of the cathodic and anodic films that will provide the desired degree of excess of the cathodic component relative to the anodic component. For example, the thickness of the desired anodic film can be determined based on one or more desired characteristics of the final end product (e.g., absorbance of the final end product at a particular wavelength) and the corresponding charge capacity at that thickness can be determined using the linear relationship illustrated in FIG. 8. In order to provide the cathodic component in excess relative to the anodic component, the data in FIG. 8 can be utilized to determine a film thickness corresponding to a particular charge capacity that is a predetermined percentage greater than the charge capacity of the anodic film. According to an aspect of the present disclosure, the thickness of the cathodic film can be selected to provide a charge capacity that is a predetermined amount greater than the anodic film. The increase in charge capacity of the cathodic component relative to the anodic component can be based on a number of factors, including the performance of the device, cost and availability of materials, physical limitations on film thickness, etc. With respect to the exemplary materials of Examples 1-3, the cathodic film thickness can be selected to provide a charge capacity that is from about 1% to about 60%, about 1% to about 50%, about 1% to about 40%, about 1% to about 30%, about 1% to about 20%, about 1% to about 10%, about 1% to about 5%, about 5% to about 60%, about 5% to about 50%, about 5% to about 40%, about 5% to about 30%, about 10% to about 60%, about 10% to about 50%, about 10% to about 40%, about 10% to about 30%, about 15% to about 60%, about 15% to about 50%, about 15% to about 40%, about 15% to about 30%, about 20% to about 60%, about 20% to about 50%, about 20% to about 40%, about 20% to about 30%, about 30% to about 60%, about 30% to about 50%, about 30% to about 40%, about 40% to about 60%, about 40% to about 50%, about 50% to about 60%, about 1% to about 25%, about 5% to about 25%, about 10% to about 25%, about 15% to about 25%, about 20% to about 25%, about 5% to about 20%, about 5% to about 15%, about 10% to about 20%, about 5%, about 10%, about 15%, about 20%, or about 25% greater than the charge capacity of the anodic component, based on the desired thickness of the anodic component.

Example 4

Figure 4B:
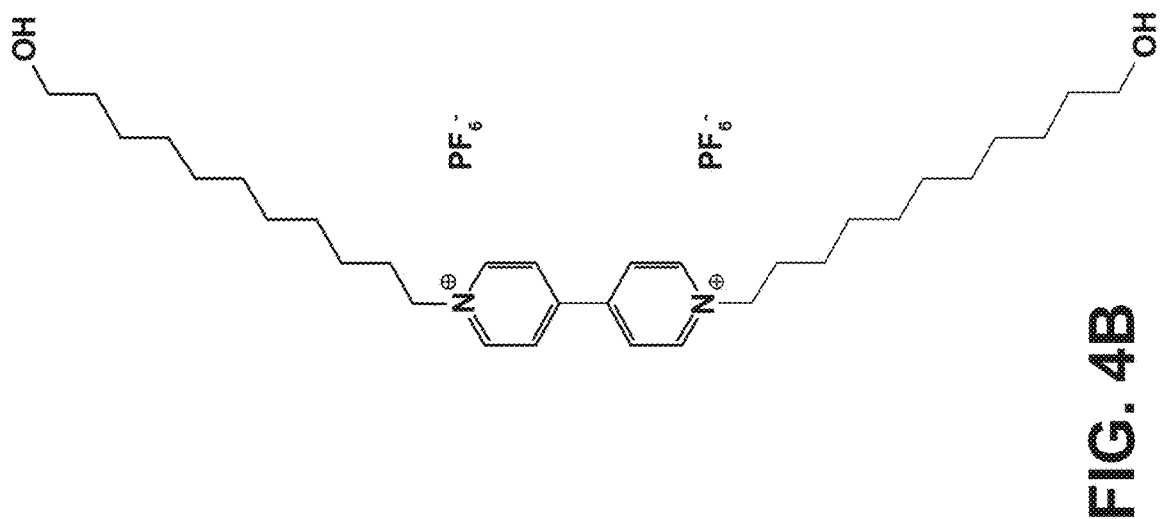
FIG. 4B illustrates the chemical structure of a cathodic component, according to an aspect of the present disclosure.

FIG. 4B illustrates the chemical structure of an exemplary cathodic component according to an aspect of the present disclosure, referred to as $VC_{11}PF_6$. The cathodic component of FIG. 4B is a viologen-based material having two $C_{11}$ alkyl alcohol function groups. These functional groups can react with an appropriate polymer matrix or multi-functional cross-linking agent to form a cross-linked cathodic film. The exemplary cathodic component $VC_{11}PF_6$ can be utilized in any of the electro-optic elements and with any of the anodic components described in the present disclosure.

The following non-limiting aspects are encompassed by the present disclosure. To the extent not already described, any one of the features of the following aspects may be combined in part or in whole with features of any one or more of the other aspects of the present disclosure to form additional aspects, even if such a combination is not explicitly described.

According to a first aspect of the present disclosure, an electro-optic element includes a cathodic film including a cathodic component sequestered adjacent to a first electrically conductive layer by a first polymer matrix and an anodic film including an anodic component sequestered adjacent to a second electrically conductive layer by a second polymer matrix. At least one of the cathodic film and the anodic film is capable of reversibly attenuating transmittance of light having a wavelength within a predetermined wavelength range.

The electro-optic element according to the first aspect, wherein the cathodic film and anodic film are configured such that the cathodic component is present in excess relative to the anodic component.

The electro-optic element according to the first aspect or any intervening aspects, wherein the cathodic component is one of confined within the first polymer matrix or covalently bonded to the first polymer matrix and the anodic component is one of confined within the second polymer matrix or covalently bonded to the second polymer matrix.

The electro-optic element according to the first aspect or any intervening aspects, wherein at least one of: the cathodic component is covalently bonded to the first polymer matrix through at least one linkage and the anodic component is covalently bonded to the second polymer matrix through at least one linkage.

The electro-optic element according to the first aspect or any intervening aspects, wherein a charge capacity of the cathodic film is greater than a charge capacity of the anodic film.

The electro-optic element according to the first aspect or any intervening aspects, wherein the charge capacity of the cathodic film is greater than the charge capacity of the anodic film by about 1% to about 60%.

The electro-optic element according to the first aspect or any intervening aspects, wherein a ratio of a molar amount of the cathodic component in the cathodic film to a molar amount of the anodic component in the anodic film is greater than 1.

The electro-optic element according to the first aspect or any intervening aspects, wherein the ratio of a molar amount of the cathodic component in the cathodic film to a molar amount of the anodic component in the anodic polymer film is in the range of about 1.01:1 to about 5:1.

The electro-optic element according to the first aspect or any intervening aspects, wherein the cathodic component includes at least one material selected from a viologen, viologen derivative, low-dimerizing viologen, non-dimerizing viologen, di-acrylate viologen, di-vinyl viologen, di-vinyl ether viologen, di-epoxy viologen, di-oxetane viologen, di-alcohol viologen, ferrocenium, ferrocenium derivative, or combinations thereof.

The electro-optic element according to the first aspect or any intervening aspects, wherein the anodic component includes at least one material selected from a phenoxazine, phenoxazine derivative, phenazine, phenazine derivative, phenothiazine, phenothiazine derivative, triphenodithiazine, triphenodithiazine derivative, carbazole, carbazole derivative, indolocarbazole, indolocarbazole derivative, biscarbazole, biscarbazole derivative, ferrocene, ferrocene derivative, 5, 10-di-(vinyl-ether)-5,10-dihydrophenazine, 5, 10-di-(vinyl)-5,10-dihydrophenazine, 5, 10-di-(acrylate)-5,10-dihydrophenazine, 5,10-di-(methacrylate)-5,10-dihydrophenazine, 5, 10-di-(epoxy)-5,10-dihydrophenazine, 5, 10-di-(oxetane)-5,10-dihydrophenazine, 5,10-di-(alcohol)-5,10-dihydrophenazine, 5, 10-dimethyl-5,10-dihydrophenazine-2, 7-di-(vinyl ether), 5, 10-dimethyl-5,10-dihydrophenazine-2, 7-di-(vinyl), 5, 10-dimethyl-5,10-dihydrophenazine-2, 7-di-(acrylate), 5,10-dimethyl-5,10-dihydrophenazine-2,7-di-(methacrylate), 5, 10-dimethyl-5, 10-dihydrophenazine-2, 7-di-(epoxy), 5, 10-dimethyl-5,10-dihydrophenazine-2, 7-di-(oxetane), 5,10-dimethyl-5,10-dihydrophenazine-2,7-di-(alcohol), 7,14-dimethyl-7,14-dihydro benzo[5,6][1,4]thiazino[2,3-b]phenothiazine-3,10-di-(vinyl ether), 7,14-dimethyl-7,14-dihydrobenzo[5,6][1,4]thiazino[2,3-b]phenothiazine-3,10-di-(vinyl), 7,14-dimethyl-7,14-dihydrobenzo[5,6][1,4]thiazino[2,3-b]phenothiazine-3,10-di-(acrylate), 7,14-dimethyl-7,14-dihydrobenzo[5,6][1,4]thiazino[2,3-b]phenothiazine-3,10-di-(methacrylate), 7,14-dimethyl-7,14-dihydrobenzo[5,6][1,4]thiazino[2,3-b]phenothiazine-3,10-di-(epoxy), 7,14-dimethyl-7,14-dihydro benzo[5,6][1,4]thiazino[2,3-b]phenothiazine-3,10-di-(oxetane), 7,14-dimethyl-7,14-dihydrobenzo[5,6][1,4]thiazino[2,3-b]phenothiazine-3,10-di-(dihydroxy), or combinations thereof.

The electro-optic element according to the first aspect or any intervening aspects, wherein at least one of the first polymer matrix, the second polymer matrix, or both includes a material selected from a solid polymer, gel polymer, polyacrylate-based polymer, polymethacrylate-based polymer, polyether-based polymer, polyester-based polymer, polycarbonate-based polymer, polyurethane-based polymer, polysiloxane-based polymer, polysilane-based polymer, polyacrylonitrile-based polymer, polystyrene-based polymer, polymethacrylonitrile-based polymer, polyamide-based polymer, polyimide-based polymer, polyvinylidene-halide-based polymer, or co-polymers or combinations of any two or more thereof.

The electro-optic element according to a first aspect or any intervening aspects, wherein the cathodic component and the anodic component each include at least a second oxidation state, and wherein the second oxidation state of the cathodic component is less stable than the second oxidation state of the anodic component.

The electro-optic element according to a first aspect or any intervening aspects, further comprising an electrolyte layer disposed between the cathodic component and the anodic component.

An electro-optic element according to a second aspect of the present disclosure includes a first electroactive film including a first electroactive component sequestered adjacent to a first electrically conductive layer, wherein the first electroactive component includes a first oxidation state and at least a second oxidation state and a second electroactive film including a second electroactive component sequestered adjacent to a second electrically conductive layer. At least one of the first electroactive film and the second electroactive film is capable of reversibly attenuating transmittance of light having a wavelength within a predetermined wavelength range, and wherein an amount of the first electroactive component relative to the second electroactive component is configured to limit formation of the second oxidation state of the first electroactive component.

The electro-optic element according to the second aspect of the present disclosure, wherein the second electroactive component includes at least a second oxidation state, and wherein the second oxidation state of the first electroactive component is less stable than the second oxidation state of the second electroactive component.

The electro-optic element according to the second aspect or any intervening aspects of the present disclosure, wherein the first or second electroactive component includes a cathodic component selected from a viologen, viologen derivative, low-dimerizing viologen, non-dimerizing viologen, di-methacrylate viologen, di-acrylate viologen, di-vinyl viologen, di-vinyl ether viologen, di-epoxy viologen, di-oxetane viologen, di-alcohol viologen, ferrocenium, ferrocenium derivative, or combinations thereof.

The electro-optic element according to the second aspect of the present disclosure or any intervening aspects, wherein the first or second electroactive component includes an anodic component selected from a phenoxazine, phenoxazine derivative, phenazine, phenazine derivative, phenothiazine, phenothiazine derivative, triphenodithiazine, triphenodithiazine derivative, carbazole, carbazole derivative, indolocarbazole, indolocarbazole derivative, biscarbazole, biscarbazole derivative, ferrocene, ferrocene derivative, 5, 10-di-(vinyl-ether)-5,10-dihydrophenazine, 5, 10-di-(vinyl)-5,10-dihydrophenazine, 5, 10-di-(acrylate)-5,10-dihydrophenazine, 5,10-di-(methacrylate)-5,10-dihydrophenazine, 5, 10-di-(epoxy)-5,10-dihydrophenazine, 5, 10-di-(oxetane)-5,10-dihydrophenazine, 5,10-di-(alcohol)-5,10-dihydrophenazine, 5, 10-dimethyl-5,10-dihydrophenazine-2, 7-di-(vinyl ether), 5, 10-dimethyl-5,10-dihydrophenazine-2, 7-di-(vinyl), 5, 10-dimethyl-5,10-dihydrophenazine-2, 7-di-(acrylate), 5,10-dimethyl-5,10-dihydrophenazine-2,7-di-(methacrylate), 5, 10-dimethyl-5,10-dihydrophenazine-2, 7-di-(epoxy), 5, 10-dimethyl-5,10-dihydrophenazine-2, 7-di-(oxetane), 5,10-dimethyl-5,10-dihydrophenazine-2,7-di-(alcohol), 7,14-dimethyl-7,14-dihydrobenzo[5,6][1,4]thiazino[2,3-b]phenothiazine-3,10-di-(vinyl ether), 7,14-dimethyl-7,14-dihydrobenzo[5,6][1,4]thiazino[2,3-b]phenothiazine-3,10-di-(vinyl), 7,14-dimethyl-7,14-dihydrobenzo[5,6][1,4]thiazino[2,3-b]phenothiazine-3,10-di-(acrylate), 7,14-dimethyl-7,14-dihydrobenzo[5,6][1,4]thiazino[2,3-b]phenothiazine-3,10-di-(methacrylate), 7,14-dimethyl-7,14-dihydrobenzo[5,6][1,4]thiazino[2,3-b]phenothiazine-3,10-di-(epoxy), 7,14-dimethyl-7,14-dihydrobenzo[5,6][1,4]thiazino[2,3-b]phenothiazine-3,10- di-(oxetane), 7,14-dimethyl-7,14-dihydrobenzo[5,6][1,4]thiazino[2,3-b]phenothiazine-3,10-di-(dihydroxy), or combinations thereof.

The electro-optic element according to the second aspect of the present disclosure or any intervening aspects, wherein the first electroactive component is one of confined within a first polymer matrix or covalently bonded to a first polymer matrix adjacent to the first electrically conductive layer and the second electroactive component is one of confined within the second polymer matrix or covalently bonded to the second polymer matrix adjacent to the second electrically conductive layer.

The electro-optic element according to the second aspect of the present disclosure or any intervening aspects, wherein at least one of: the first electroactive component is covalently bonded to the first polymer matrix through at least one linkage and the second electroactive component is covalently bonded to the second polymer matrix through at least one linkage.

The electro-optic element according to the second aspect of the present disclosure or any intervening aspects, wherein at least one of the first polymer matrix, the second polymer matrix, or both includes a material selected from a solid polymer, gel polymer, polyacrylate-based polymer, polymethacrylate-based polymer, polyether-based polymer, polyester-based polymer, polycarbonate-based polymer, polyurethane-based polymer, polysiloxane-based polymer, polysilane-based polymer, polyacrylonitrile-based polymer, polystyrene-based polymer, polymethacrylonitrile-based polymer, polyamide-based polymer, polyimide-based polymer, polyvinylidenehalide-based polymer, or co-polymers or combinations of any two or more thereof.

The electro-optic element according to the second aspect of the present disclosure or any intervening aspects, wherein a charge capacity of the first electroactive film is greater than a charge capacity of the second electroactive film.

The electro-optic element according to the second aspect of the present disclosure or any intervening aspects, wherein the charge capacity of the first electroactive film is greater than the charge capacity of the second electroactive film by about 1% to about 60%.

The electro-optic element according to the second aspect of the present disclosure or any intervening aspects, wherein a ratio of a molar amount of the first electroactive component in the first electroactive film to a molar amount of the second electroactive component in the second electroactive film is greater than 1.

A method of forming an electro-optic element according to a third aspect of the present disclosure includes: providing a first electroactive film including a first electroactive component sequestered adjacent to a first electrically conductive layer, wherein the first electroactive component includes a first oxidation state and at least a second oxidation state; providing a second electroactive film including a second electroactive component sequestered adjacent to a second electrically conductive layer; and providing an amount of the first electroactive component relative to the second electroactive component that is configured to limit formation of the second oxidation state of the first electroactive component. At least one of the first electroactive film and the second electroactive film is capable of reversibly attenuating transmittance of light having a wavelength within a predetermined wavelength range.

The electro-optic element according to the third aspect of the present disclosure, wherein the second electroactive component includes at least a second oxidation state, and wherein the second oxidation state of the first electroactive component is less stable than the second oxidation state of the second electroactive component.

The method according to the third aspect of the present disclosure, wherein the step of providing an amount of the first electroactive component relative to the second electroactive component includes at least one of: providing the first electroactive film with a charge capacity greater than the second electroactive film; providing the first electroactive film with a film thickness that is greater than a film thickness of the second electroactive film; and providing the first and second electroactive films such that a ratio of a molar amount of the first electroactive component to a molar amount of the second electroactive component is greater than 1.

The method according to the third aspect of the present disclosure or any intervening aspects, wherein the step of providing a first electroactive film and the step of providing a second electroactive film includes: providing a first electroactive component that is one of confined within a first polymer matrix or covalently bonded to a first polymer matrix and providing a second electroactive component that is one of confined within a second polymer matrix or covalently bonded to a second polymer matrix.

The method according to the third aspect of the present disclosure or any intervening aspects, wherein at least one of: the first electroactive component is covalently bonded to the first polymer matrix through at least one linkage and the second electroactive component is covalently bonded to the second polymer matrix through at least one linkage.

The method according to the third aspect of the present disclosure or any intervening aspects, wherein at least one of the first polymer matrix, the second polymer matrix, or both includes a material selected from a solid polymer, gel polymer, polyacrylate-based polymer, polymethacrylate-based polymer, polyether-based polymer, polyester-based polymer, polycarbonate-based polymer, polyurethane-based polymer, polysiloxane-based polymer, polysilane-based polymer, polyacrylonitrile-based polymer, polystyrene-based polymer, polymethacrylonitrile-based polymer, polyamide-based polymer, polyimide-based polymer, polyvinylidenehalide-based polymer, or co-polymers or combinations of any two or more thereof.

The method according to the third aspect of the present disclosure or any intervening aspects, wherein the first or second electroactive material includes a cathodic component selected from a viologen, viologen derivative, low-dimerizing viologen, non-dimerizing viologen, di-methacrylate viologen, di-acrylate viologen, di-vinyl viologen, di-vinyl ether viologen, di-epoxy viologen, di-oxetane viologen, di-alcohol viologen, ferrocenium, ferrocenium derivative, or combinations thereof.

The method according to the third aspect of the present disclosure or any intervening aspects, wherein the first or second electroactive material includes an anodic component selected from a phenoxazine, phenoxazine derivative, phenazine, phenazine derivative, phenothiazine, phenothiazine derivative, triphenodithiazine, triphenodithiazine derivative, carbazole, carbazole derivative, indolocarbazole, indolocarbazole derivative, biscarbazole, biscarbazole derivative, ferrocene, ferrocene derivative, 5, 10-di-(vinylether)-5,10-dihydrophenazine, 5, 10-di-(vinyl)-5,10-dihydrophenazine, 5, 10-di-(acrylate)-5,10-dihydrophenazine, 5,10-di-(methacrylate)-5,10-dihydrophenazine, 5, 10-di-(epoxy)-5,10-dihydrophenazine, 5, 10-di-(oxetane)-5,10-dihydrophenazine, 5,10-di-(alcohol)-5,10-dihydrophenazine, 5, 10-dimethyl-5,10-dihydrophenazine-2, 7-di-(vinyl ether), 5, 10-dimethyl-5,10-dihydrophenazine-2, 7-di-(vinyl), 5, 10-dimethyl-5,10-dihydrophenazine-2, 7-di-(acrylate), 5,10-dimethyl-5,10-dihydrophenazine-2,7-di-(methacrylate), 5, 10-dimethyl-5,10-dihydrophenazine-2, 7-di-(epoxy), 5, 10-dimethyl-5,10-dihydrophenazine-2, 7-di-(oxetane), 5,10-dimethyl-5,10-dihydrophenazine-2,7-di-(alcohol), 7,14-dimethyl-7,14-dihydrobenzo[5,6][1,4]thiazino[2,3-b]phenothiazine-3,10-di-(vinyl ether), 7,14-dimethyl-7,14-dihydrobenzo[5,6][1,4]thiazino[2,3-b]phenothiazine-3,10-di-(vinyl), 7,14-dimethyl-7,14-dihydrobenzo[5,6][1,4]thiazino[2,3-b]phenothiazine-3,10-di-(acrylate), 7,14-dimethyl-7,14-dihydrobenzo[5,6][1,4]thiazino[2,3-b]phenothiazine-3,10-di-(methacrylate), 7,14-dimethyl-7,14-dihydrobenzo[5,6][1,4]thiazino[2,3-b]phenothiazine-3,10-di-(epoxy), 7,14-dimethyl-7,14-dihydrobenzo[5,6][1,4]thiazino[2,3-b]phenothiazine-3,10-di-(oxetane), 7,14-dimethyl-7,14-dihydrobenzo[5,6][1,4]thiazino[2,3-b]phenothiazine-3,10-di-(dihydroxy), or combinations thereof.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:

1. An electro-optic element, comprising:
   a cathodic film including a cathodic component sequestered adjacent to a first electrically conductive layer by a first polymer matrix; and
   an anodic film including an anodic component sequestered adjacent to a second electrically conductive layer by a second polymer matrix;
   wherein at least one of the cathodic film and the anodic film is capable of reversibly attenuating transmittance of light between a transparent state and a darkened state, and
   wherein the cathodic film and anodic film are configured such that a ratio of a molar amount of the cathodic component in the cathodic film to a molar amount of the anodic component in the anodic film is from greater than 1.1:1 to about 2:1.

2. The electro-optic element according to claim 1, wherein:
   the cathodic component is confined within the first polymer matrix or covalently bonded to the first polymer matrix; and
   the anodic component is confined within the second polymer matrix or covalently bonded to the second polymer matrix.

3. The electro-optic element according to claim 1, wherein a charge capacity of the cathodic film is greater than a charge capacity of the anodic film.

4. The electro-optic element according to claim 1, wherein a ratio of a molar amount of the cathodic component in the cathodic film to a molar amount of the anodic component in the anodic film is greater than 1.

5. The electro-optic element according to claim 1, wherein the cathodic component comprises at least one material selected from the group consisting of a viologen, viologen derivative, low-dimerizing viologen, non-dimerizing viologen, di-acrylate viologen, di-vinyl viologen, di-vinyl ether viologen, di-epoxy viologen, di-oxetane viologen, di-alcohol viologen, ferrocenium, and ferrocenium derivative, or combinations thereof.

6. The electro-optic element according to claim 1, wherein the anodic component comprises at least one material selected from the group consisting of a phenoxazine, phenoxazine derivative, phenazine, phenazine derivative, phenothiazine, phenothiazine derivative, triphenodithiazine, triphenodithiazine derivative, carbazole, carbazole derivative, indolocarbazole, indolocarbazole derivative, biscarbazole, biscarbazole derivative, ferrocene, ferrocene derivative, 5, 10-di-(vinyl -ether)-5,10-dihydrophenazine, 5, 10-di-(vinyl)- 5,10-dihydrophenazine, 5, 10-di-(acrylate)-5,10-dihydrophenazine, 5,10-di-(methacrylate)-5,10-dihydrophenazine, 5, 10-di-(epoxy)-5,10-dihydrophenazine, 5, 10-di-(oxetane)- 5,10-dihydrophenazine, 5,10-di-(alcohol)-5,10-dihydrophenazine, 5, 10-dimethyl-5,10-dihydrophenazine-2, 7-di-(vinyl ether), 5, 10-dimethyl-5,10-dihydrophenazine-2, 7-di-(vinyl), 5, 10-dimethyl-5,10-dihydrophenazine-2, 7-di-(acrylate), 5,10-dimethyl-5,10-dihydrophenazine-2,7-di-(methacrylate), 5, 10-dimethyl-5, 10-dihydrophenazine-2, 7-di-(epoxy), 5, 10-dimethyl-5,10-dihydrophenazine-2, 7-di-(oxetane), 5,10-dimethyl-5,10-dihydrophenazine-2,7-di-(alcohol), 7,14-dimethyl-7,14-dihydrobenzo[5,6][1,4]thiazino[2,3-b]phenothiazine-3,10-di-(vinyl ether), 7,14-dimethyl-7,14-dihydrobenzo[5,6][1,4]thiazino[2,3-b]phenothiazine -3,10-di-(acrylate), 7,14-dimethyl-7,14-dihydrobenzo[5,6][1,4]thiazino[2,3-b]phenothiazine-3,10-di-(methacrylate), 7,14-dimethyl-7,14-dihydrobenzo[5,6][1,4]thiazino[2,3-b]phenothiazine-3,10-di-(epoxy), 7,14-dimethyl-7,14-dihydrobenzo[5,6][1,4]thiazino[2,3-b]phenothiazine-3,10-di-(oxetane), and 7,14-dimethyl-7,14- dihydrobenzo[5,6][1,4]thiazino[2,3-b]phenothiazine-3,10-di-(dihydroxy), or combinations thereof.

7. The electro-optic element according to claim 1, wherein at least one of the first polymer matrix, the second polymer matrix, or both comprises at least one material selected from the group consisting of a solid polymer, gel polymer, polyacrylate-based polymer, polymethacrylate-based polymer, polyether-based polymer, polyester-based polymer, polycarbonate-based polymer, polyurethane-based polymer, polysiloxane-based polymer, polysilane-based polymer, polyacrylonitrile-based polymer, polystyrene-based polymer, polymethacrylonitrile-based polymer, polyamide-based polymer, polyimide-based polymer, polyvinylidenehalide-based polymer, and co-polymers or combinations of any two or more thereof.

8. The electro-optic element according to claim 1, further comprising an electrolyte layer disposed between the cathodic component and the anodic component.

9. The electro-optic element according to claim 1, further comprising:
a first substrate;
a second substrate; and
a display.

10. The electro-optic element according to claim 9, further comprising:
first and second annular bands of highly conductive material, wherein the first and second annular bands are deposited around a perimeter of each of the first and second substrates, respectively, and wherein the first and second annular bands are in electrical contact with the first and second electrically conductive layers, respectively.

11. The electro-optic element according to claim 10, wherein the first and second annular bands of highly conductive material include at least one of silver, gold, and aluminum.

12. The electro-optic element according to claim 11, wherein the at least one of silver, gold, and aluminum are in a form of metallic flakes or particles dispersed in a hosting material.

13. The electro-optic element according to claim 9, wherein the first substrate is offset from the second substrate along at least a portion of a perimeter of the first substrate.

14. The electro-optic element according to claim 1, further comprising:
a polarizer.

15. The electro-optic element according to claim 14, wherein the polarizer is a wire-grid polarizer.

16. The electro-optic element according to claim 1, further comprising:
at least one solvent, wherein the at least one solvent, the anodic film, and the cathodic film at least partially form an electrochromic structure.

17. The electro-optic element according to claim 1, wherein at least one of the anodic film and the cathodic film is electrochromic.

18. An electro-optic device, comprising:
an electro-optic element operable between a clear state and a darkened state, comprising:
a first substrate having a first surface and a second surface;
a second substrate having a third surface and a fourth surface;
a first electrically conductive layer positioned on the second surface;
a second electrically conductive layer positioned on the third surface;
a cathodic film including a cathodic component sequestered adjacent to a first electrically conductive layer by a first polymer matrix, wherein the cathodic film is positioned on the first electrically conductive layer; and
an anodic film including an anodic component sequestered adjacent to a second electrically conductive layer by a second polymer matrix, wherein the anodic film is positioned on the second electrically conductive layer, wherein the cathodic film and anodic film are configured such that a ratio of a molar amount of the cathodic component in the cathodic film to a molar amount of the anodic component in the anodic film is from greater than 1.1:1 to about 5:1.

19. The electro-optic device of claim 18, wherein the ratio of the molar amount of the cathodic component in the cathodic film to the molar amount of the anodic component in the anodic film is from 1.25:1 to 4:1.

20. The electro-optic device of claim 19, wherein the ratio of the molar amount of the cathodic component in the cathodic film to the molar amount of the anodic component in the anodic film is from about 1.5:1 to about 2:1.

* * * * *